US010321292B2

(12) United States Patent
Pflugh et al.

(10) Patent No.: US 10,321,292 B2
(45) Date of Patent: Jun. 11, 2019

(54) DYNAMIC ANNOUNCING FOR CREATION OF WIRELESS COMMUNICATION CONNECTIONS

(71) Applicant: Pacesetter, Inc., Sunnyvale, CA (US)

(72) Inventors: Timothy Pflugh, Mountain View, CA (US); Fujian Qu, San Jose, CA (US); Benjamin Coppola, Solano Beach, CA (US); Edward Karst, Los Angeles, CA (US); Lisa P. Weinberg, Moorpark, CA (US); Xing Pei, Thousand Oaks, CA (US); Yongjian Wu, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 15/692,199

(22) Filed: Aug. 31, 2017

(65) Prior Publication Data

US 2017/0366921 A1 Dec. 21, 2017

Related U.S. Application Data

(63) Continuation-in-part of application No. 15/182,784, filed on Jun. 15, 2016, now Pat. No. 9,907,486.
(Continued)

(51) Int. Cl.
*H04W 4/70* (2018.01)
*A61N 1/372* (2006.01)
(Continued)

(52) U.S. Cl.
CPC .............. *H04W 4/70* (2018.02); *A61B 5/0031* (2013.01); *A61B 5/024* (2013.01);
(Continued)

(58) Field of Classification Search
CPC .......... A61B 2562/0219; A61B 5/1118; A61B 5/686; A61B 5/7275; A61B 5/7282; A61B 2503/12; A61B 5/02416; A61B 5/02438; A61B 5/0255; A61B 5/0402; A61B 5/0464; A61B 5/076; A61B 5/1116; A61B 5/743; A61B 5/0031; A61B 5/02055; A61B 5/024; A61B 5/042; A61B 5/046; A61B 5/4836;
(Continued)

(56) References Cited

U.S. PATENT DOCUMENTS 7,742,807 B1 * 6/2010 Walls .................... A61B 5/0402
600/509
8,801,624 B2 * 8/2014 Patangay ................. A61B 7/00
600/528
(Continued)

*Primary Examiner* — Nader Bolourchi
(74) *Attorney, Agent, or Firm* — Theresa Raymer

(57) ABSTRACT

Example electronic devices, including but not limited to implantable medical devices, and methods employing dynamic announcing for creation of wireless communication connections are disclosed herein. In an example, an electronic device includes a wireless communication interface to transmit announcement signals for creating a wireless communication connection with the external device. The electronic device also includes a sensor to detect a characteristic of an environment external to the electronic device, and a control circuit including an announcement timing control module to dynamically control timing of the announcement signals based on the detected characteristic.

24 Claims, 9 Drawing Sheets

Related U.S. Application Data

(60) Provisional application No. 62/339,795, filed on May 20, 2016.

(51) Int. Cl.

| | | |
|---|---|---|
| *H04L 7/00* | (2006.01) | |
| *A61B 5/00* | (2006.01) | |
| *G01D 5/249* | (2006.01) | |
| *A61B 5/0205* | (2006.01) | |
| *A61B 5/024* | (2006.01) | |
| *A61B 5/042* | (2006.01) | |
| *A61B 5/046* | (2006.01) | |
| *H04W 76/10* | (2018.01) | |
| *A61B 5/11* | (2006.01) | |

(52) U.S. Cl.
CPC .......... *A61B 5/02055* (2013.01); *A61B 5/042* (2013.01); *A61B 5/046* (2013.01); *A61B 5/4836* (2013.01); *A61B 5/686* (2013.01); *A61N 1/37254* (2017.08); *A61N 1/37258* (2013.01); *G01D 5/2492* (2013.01); *H04L 7/0087* (2013.01); *H04W 76/10* (2018.02); *A61B 5/1118* (2013.01); *A61B 5/7225* (2013.01); *A61B 5/7275* (2013.01); *A61B 5/7282* (2013.01); *A61B 2562/0219* (2013.01)

(58) Field of Classification Search
CPC ...... A61B 5/7225; H04W 76/10; H04W 4/70; G06F 19/00; A61N 1/37254; A61N 1/37258; G01D 5/2492; H04L 7/0087
See application file for complete search history.

(56) References Cited

U.S. PATENT DOCUMENTS 9,288,614 B1 *   3/2016   Young ................ A61N 1/37252
2017/0196458 A1 *   7/2017   Ternes ................ A61B 5/0031

* cited by examiner

DYNAMIC ANNOUNCING FOR CREATION OF WIRELESS COMMUNICATION CONNECTIONS

PRIORITY CLAIM

The present application is a Continuation-In-Part of U.S. patent application Ser. No. 15/182,784, filed Jun. 15, 2016, entitled "Dynamic Announcing For Creation Of Wireless Communication Connections," which claims priority to U.S. provisional application Ser. No. 62/339,795, filed May 20, 2016, entitled "Dynamic Announcing For Creation Of Wireless Communication Connections," both of which are hereby expressly incorporated by reference in their entirety to provide continuity of disclosure.

FIELD OF THE INVENTION

The present invention relates to wireless communication technology. More specifically, the present invention relates to dynamically varying announcing frequency for creation of wireless communication connections.

BACKGROUND OF THE INVENTION

Many wireless communication technology standards, such as the original Bluetooth® standard and its variants (e.g., the Bluetooth® Low Energy, or BLE, standard), facilitate creation of communication connections between pairs of devices using announcement or advertising data packets, messages, or other signals. In some communication standards, for example, an electronic device may transmit such signals wirelessly while in an announcing or advertising mode (e.g., "discoverable" mode in the Bluetooth® standard) to make nearby devices aware of the presence of the announcing device. In response to those announcements or advertisements, another device may then attempt to create a communication connection with the announcing device by way of bidirectional exchange of device identities and/or capabilities, encryption/decryption keys, and other information with the electronic device to create a secure communication connection therebetween.

Typically, an electronic device is placed into its announcing or advertising mode in response to some user input received via a user interface, such as the press of a button or touch of an area on a touchscreen. However, some electronic devices that employ a wireless communication technology either do not provide a tactile user interface, or simply cannot be accessed physically during normal operation. One such class of device is the implantable medical device. Examples of implantable medical devices include, but are not limited to, automatic implantable cardioverter defibrillators (AICDs), cardiac pacemakers, spinal cord stimulation (SCS) devices, deep brain stimulation (DBS) devices, and implantable loop recorders (ILRs), such as implantable cardiac monitors (ICMs) and subcutaneous atrial fibrillation (AF) monitors. Such devices often employ wireless communication to connect with an external computer system to receive configuration information, commands, and so on, and to transmit operational status, logged events, and the like. Such devices, when implanted in a human body, are not physically accessible, nor preferable using physical external input such as pressure with tapping, and thus do not provide a tactile or physical interface to facilitate placing the device into an announcing or advertising mode to establish wireless communication with another device.

With the above aspects in mind, as well as others not explicitly discussed herein, various embodiments of an electronic device employing wireless communication, such as an implantable medical device, as well as methods of operating such a device, are disclosed herein.

SUMMARY

In one embodiment, an electronic device may include a wireless communication interface to transmit announcement signals for creating a wireless communication connection with an external device separate from the electronic device. The electronic device may also include a sensor to detect a characteristic of an environment external to the electronic device, and a control circuit including an announcement timing control module that is configured to access one or more announcement factors based on the detected characteristic and to dynamically control timing (e.g., frequency) of the announcement signals based on the one or more announcement factors and the detected characteristic. In some examples, the electronic device may be an implantable medical device.

Optionally, the electronic device may comprise at least one of an automatic implantable cardioverter defibrillator, an artificial cardiac pacemaker, and an implantable loop recorder. The detected characteristic may comprise an electrical signal produced by a heart of a patient. The detected characteristic may comprise a signal indicative of a patient's heart activity. A real-time clock may be configured to provide a current time of day. The announcement timing control module may further be configured to dynamically control timing of the announcement signals based on both the detected characteristic and on the current time of day. The sensor may be at least one of an accelerometer and a gyroscope. The detected characteristic may be is a signal indicative of an activity level of a human.

Optionally, the announcement timing control module may be configured to lower the frequency of announcement signals when the current time of day is an expected time of sleep and the activity level is indicative of a supine posture. The announcement timing control module may be configured to access one or more announcement factors based on the detected characteristic. The announcement factors may represent at least one of a clinical condition or a system condition. The clinical condition may represent at least one of a ventricular fibrillation (VF) episode, a high voltage shock, a major ischemic event, or a device delivery of a patient notification. The announcement timing control module may be configured to at least one of i) increase an advertising frequency, increase a number of advertising pulses per advertising cycle, or decrease a pulse to pulse interval during the advertising cycle.

In accordance with embodiments herein, an implantable medical device is provided for monitoring physiology of a person. The implantable medical device is capable of wirelessly communicating with an external device located external to the person. The implantable medical device comprises a wireless communication interface configured to transmit announcement signals for creating a wireless communication connection with the external device, at least one sensor configured to detect a characteristic of an environment external to the implantable medical device and a control circuit comprising an announcement timing control module configured to access one or more announcement factors based on the detected characteristic and to dynamically control timing of the announcement signals based on at least the one or more announcement factors and the detected characteristic.

Optionally, the announcement signals may comprise announcement messages that may be configured to dynamically vary the discovery opportunities of the implantable medical device by the external device in a manner that will reduce current drain. The announcement timing control module may be configured to dynamically control the timing of the announcement messages by dynamically setting a frequency at which the announcement messages are repeatedly transmitted based on at least the detected characteristic. The announcement timing control module may be configured to dynamically set the frequency to at least one of a first frequency, and a second frequency slower than the first frequency. The implantable medical device may comprise a heart activity detector that may be configured to determine a heart activity of the person based on the detected characteristic. The announcement timing control module may be configured to dynamically increase or decrease the frequency of the announcement messages based on the heart activity.

Optionally, the implantable medical device may be configured to determine a heart rate of the person based on the detected characteristic. The announcement timing control module may be configured to increase the frequency of the announcement messages in response to the determined heart rate exceeding a first threshold or falling below a second threshold. The implantable medical device may be configured to determine a body position, a physical activity level of the person and whether the physical activity level of the person exceeds a threshold. The announcement timing control module may be configured to increase the frequency of the announcement messages in response to the determined body position being an upright position, and the determined physical activity level of the person exceeding a threshold. The implantable medical device may be configured to determine a body position, and a physical activity level of the person. The announcement timing control module may be configured to cease transmission of the announcement messages in response to the determined body position, and the determined physical activity level of the person indicating that the person is sleeping.

Optionally, the heart activity detector may further be configured to detect an arrhythmia. The implantable device may be configured to determine at least one of a body position and a physical activity level of the person. The announcement timing control module may be further configured to determine whether the arrhythmia and the, at least one, body position and physical activity level of the person indicate an exercise-induced arrhythmia and increase the frequency of the announcement messages when an exercise-induced arrhythmia is determined. A real-time clock may be configured to provide a current time of day. The announcement timing control module may be configured to dynamically set the frequency of the announcement messages based on the current time of day. The announcement timing control module may be configured to predict times to change timing of the announcement signals based on the detected characteristic. The announcement timing control module may be configured to predict the time by identifying a pattern associating user-initiated sessions and occurrence of a clinical condition and based on the pattern, designate the clinical condition to represent the detected characteristic.

Optionally, a heart activity detector may be configured to determine a heart activity of the person based on the detected characteristic. A memory may be configured to store a heart activity together with the time of day at which the heart activity was detected and a microcontroller may be configured to determine a trend in the time of day at which pathological heart activity is detected. The announcement timing control module may be further configured to dynamically set the frequency of the announcement messages based the trend. A heart activity detector may be configured to determine a heart activity of the person and determine whether the heart activity is a pathological heart activity based on the detected characteristic. An event detector may be configured to detect a cardiac event. A memory may be configured to store at least one of the pathological heart activity and the cardiac event together with the time of day at which at least one of the pathological heart activity and the cardiac event was detected. A microcontroller may be configured to determine a trend in the time of day at which at least one of the pathological heart activity and cardiac event is detected. The announcement timing control module may be further configured to dynamically set the frequency of the announcement messages based on the trend.

Optionally, a heart activity detector may be configured to determine a heart activity of the person based on the detected characteristic. An event detector may be configured to detect cardiac events. A memory may be configured to store at least one of the heart activity and cardiac event when the person triggers the implantable medical device to connect with an external device. A microcontroller may be configured to determine a trend in at least one of the heart activity and the cardiac event occurring when the person triggers the implantable medical device to connect with the external device. The announcement timing control module may be further configured to increase the frequency of the announcement messages when at least one of a current detected heart activity and a current detected cardiac event satisfies the trend. A sensor may be configured to detect a level of acceleration imparted upon the implantable medical device. The announcement timing control module may be configured to increase the frequency of the announcement messages based on the detected level of acceleration exceeding a threshold.

In accordance with embodiments herein, a method is provided for dynamically controlling a frequency of advertising messages transmitted by an electronic device to create a wireless communication connection with an external device separate from the electronic device. The method detects a characteristic of an environment external to the electronic device, accesses an announcement frequency factor employable to set a frequency of advertising messages. The announcement frequency factor is based on the detected characteristic. The method sets at least one of a frequency of the advertising messages, a number of advertising pulses per advertising cycle or a pulse to pulse interval during the advertising cycle, based at least in part on the announcement frequency factor and transmits the advertising messages using the frequency.

Optionally, the announcement frequency factor may comprise at least one of a heart rate of a patient, a clinical condition, a system condition, at least one of a cardiac and neurogenic event of a patient or at least one of a body position any a physical activity level of a patient. The method may provide a current time of day using a real-time clock, wherein setting a frequency of the advertising messages based at least in part on the announcement frequency factor.

While multiple embodiments are disclosed, still other embodiments of the present invention will become apparent to those skilled in the art from the following detailed description, which depicts and describes illustrative embodiments of the invention. As will be realized, the invention is capable of modifications in various aspects, all without departing from the scope of the present invention. Accordingly, the drawings and detailed description are to be regarded as illustrative in nature and not restrictive.

DETAILED DESCRIPTION

Figure 1:
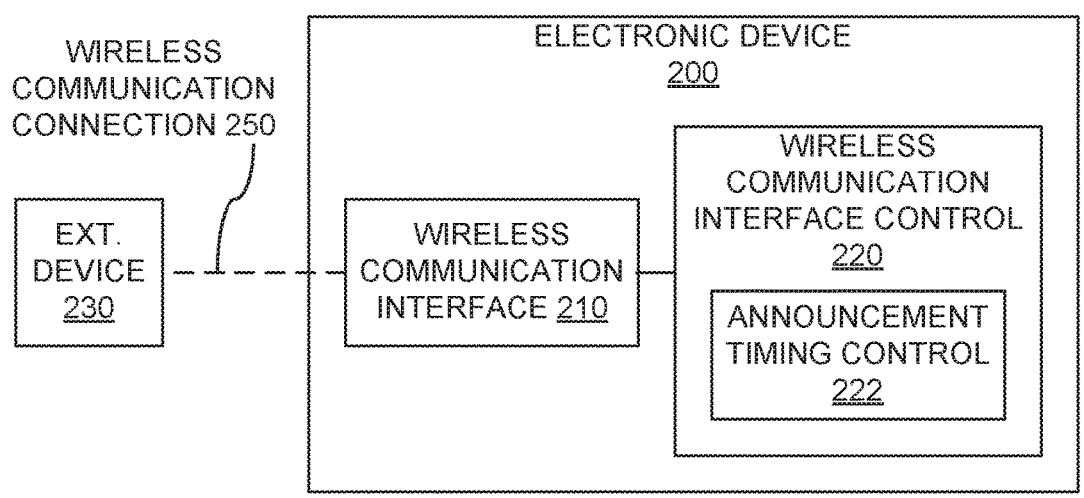
FIG. 1 is a simplified block diagram of an example electronic device that employs dynamic announcing for creation of wireless communication connections.

This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

The following detailed description relates to electronic devices that employ a wireless communication interface. In one example, an electronic device may employ dynamic advertising (referred to herein as "announcing") for creation of wireless communication connections with one or more other devices external to the electronic device via the wireless interface. In one example, the electronic device may alter the frequency of announcement messages, data packets, or other signals that are used to create a wireless communication connection. Alteration of the frequency may be based on one or more announcement frequency (AF) factors that may be accessed or sensed by the electronic device. In at least some examples, the electronic device may be an implantable medical device, such as an automatic implantable cardioverter defibrillator (AICD), pacemaker, spinal cord stimulation (SCS) system, deep brain stimulation (DBS) system, implantable loop recorder, or the like. In at least some examples, the external device may be a smartphone, smartwatch, personal digital assistant (PDA), tablet, laptop computer, desktop computer, bedside monitor, programmer, or the like.

As a result of at least some of the embodiments discussed in greater detail below, the electronic device may alter the frequency at which announcement messages or other signals are issued to balance overall power consumption of the device with the amount of time consumed in establishing a wireless communication connection when a physical user interface to the device (e.g., a button, a touchscreen, or the like) is non-existent or limited, thus at least restricting the ability of a user to place the device in an announcement mode explicitly. More specifically, announcement messages issued more often would reduce the amount of time to create a communication connection while increasing power consumption, whereas issuing such messages less often would tend to produce the opposite effects.

In some devices currently employing Bluetooth® technology, a user may initiate the formation of a connection between devices by making at least one of those devices "discoverable" by causing that device to transmit or broadcast one or more announcement or advertisement messages. Such initiation may be in the form of a press of a button, a touch of a touchscreen area, or other direct physical contact with the device. The announcement messages may include some identification information of the device, some encryption key information, and/or so forth. A nearby device, in response to receiving one of the announcements, may "pair" with the device providing the announcement messages to exchange further encryption information, data regarding capabilities of the two devices, and so on. Based on that exchange of information, the two devices may then be "bonded" to each other, facilitating one or more wireless communication connections between the devices over any arbitrary time period until the devices are unbonded.

Further, some devices provide a Bluetooth® pairing mechanism by way of the Near Field Communications (NFC) technology protocol. In such cases, a user may bring a Bluetooth® device into contact or near-contact with another Bluetooth® device to pair the devices without the use of an explicit announcement message phase.

In the situations described above, physical contact or near-contact with a device by way of a user or another device is utilized to initiate a process by which wireless communications are established between devices. In examples described more fully below, however, wireless communication connections may be facilitated without such interaction.

FIG. 1 is a simplified block diagram of an example electronic device 200 that employs dynamic announcing for creation of wireless communication connections. In this example, the electronic device 200 includes a wireless communication interface 210 that may transmit wireless communication signals to, and/or receive wireless communication signals from, an external device 230, such as by way of an established wireless communication connection 250. The wireless communication interface 210 may include wireless signal transmitters, wireless signal receivers, and/or other circuitry for providing functionality. In one example, the wireless signals conform to a wireless communication standard, such as Bluetooth®, Bluetooth® Low Energy (BLE), ZigBee®, IEEE (Institute of Electrical and Electronics Engineers) 802.15.4, MICS (Medical Implant Communication Service), MedRadio (Medical Device Radiocommunications Service), or any other wireless communication standard that employs presence announcing or advertising to enable communication between at least two devices, such as by way of establishing a wireless communication connection between the electronic device 200 and the external device 230. U.S. Pat. No. 9,288,614 (Young et. al) and U.S. Pub. No. 2015/0065047 (Wu et al.), each of which is incorporated herein by reference in its entirety, describe exemplary systems and methods that may be used in conjunction with the present invention to provide for initiating a bidirectional wireless communication connection 250 between electronic device 200 and external device 230.

As depicted in FIG. 1, the electronic device 200 may also include a wireless communication interface control module 220 that may provide logic and control functions to operate the wireless communication interface 210 according to the protocols or standards being used to perform the desired wireless communications. For example, the wireless communication interface control module 220 may provide the logic for performing the announcement messages, pairing, bonding, and connection creation of the Bluetooth® standards, as described above. In some examples, the wireless communication interface control module 220 may include dedicated hardware circuitry to perform the desired functions. In other examples, the wireless communication interface control module 220 may include one or more hardware processors, such as microprocessors, microcontrollers, digital signal processors (DSPs), or other algorithmic processors, along with one or more memory devices containing instructions executable by the one or more hardware processors, to perform the functions ascribed to the wireless communication interface control module 220. In yet other embodiments, the wireless communication interface control module 220 may include some combination of dedicated hardware circuitry and programmable hardware processor components.

Included within the wireless communication interface control module 220 may be an announcement timing control module 222, which may access one or more AF factors that indicate one or more characteristics of the environment in which the electronic device 200 operates to determine dynamically when or how often one or more announcing or advertising messages, data packets, or other signals are to be transmitted to facilitate creation of one or more wireless communication connections 250 between the electronic device 200 and the external device 230.

External device 230 may include a patient activator to enable the user, such as a patient or caregiver, to manually trigger electronic device 200 either to trigger an alert or trigger recording of EGM storage or other clinical episode, such as an episode of neuropathic pain, palpitations, or syncope.

Figure 2:
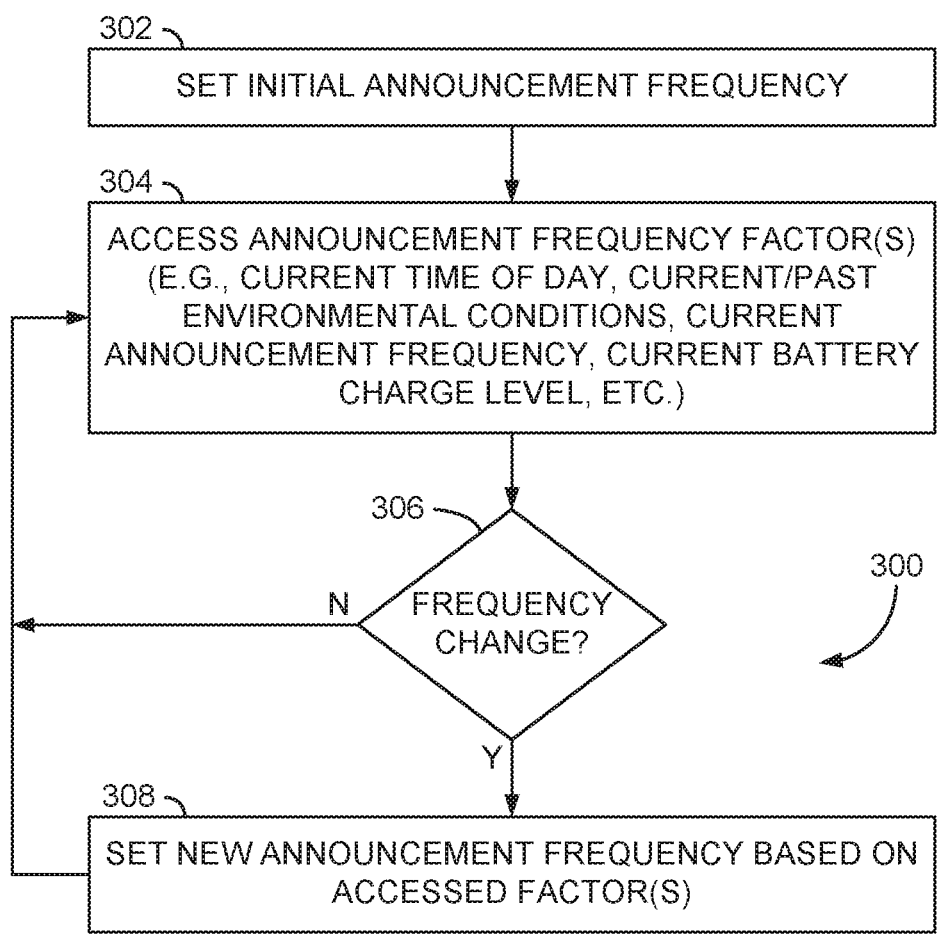
FIG. 2 is a simplified flow diagram of an example method of operating the electronic device of FIG. 1 to employ dynamic announcing for creation of wireless communication connections.

FIG. 2 is a simplified flow diagram 300 of an example method 300 of operating an electronic device (e.g., the electronic device 200 of FIG. 1) to employ dynamic announcing for creation of wireless communication connections (e.g., the wireless communication connection 250 of FIG. 1). While the method 300 is described below within the context of the announcement timing control module 222 of the wireless communication interface control module 220 of the electronic device 200 of FIG. 1, other circuits or systems may employ the method 300 in other embodiments.

In the method 300, the announcement timing control module 222 may set an initial frequency for transmission of announcement messages, data packets, or other signals (operation 302). In some examples, the frequency may be once every so many seconds or minutes, or may be zero (e.g., no announcement messages) for at least some periods of time. However, in other examples, the announcement timing control module 222 may not set an initial transmission frequency for the announcements.

Thereafter, the announcement timing control module 222 may access one or more AF factors that are to influence dynamically the frequency of the announcements (operation 304). The announcement frequency may be dynamically adjusted for one or more of i) a frequency at which advertisement periods/cycles are transmitted ii) a number of advertisement pulses transmitted during an announcement period/cycle and/or iii) a pulse to pulse interval between successive advertising pulses in one announcement period/cycle. For example, the announcement frequency may be determined to transmit X advertising pulses (spaced apart by a pulse to pulse interval Y) every Z minutes. The frequency at which advertisement periods/cycles are repeated may be changed alone or in combination with other adjustments as the dynamic adjustment of the announcement frequency. The number X advertising pulses that are transmitted during one period/cycle of the announcement frequency may be changed alone or in combination with other adjustments as the dynamic adjustment of the announcement frequency. The pulse to pulse interval between the advertising pulses within an individual period/cycle may be changed alone or in combination with other adjustments as the dynamic adjustment of the announcement frequency.

Examples of such AF factors may include, but are not limited to, the current time of day, current and/or past environmental and/or operational conditions in which the electronic device 200 is operating, the current announcement frequency, the current charge level of a battery or other energy source being employed by the electronic device 200 to perform its various functions, and so forth. Other AF factors, such as those that may be related to the specific operations performed by the electronic device 200, may be utilized in other embodiments. The announcement timing control module 222 may then determine whether a change in the announcement frequency is warranted based on the accessed AF factors (operation 306). If so, the announcement timing control module 222 sets a new, modified announcement frequency based on the accessed factors (operation 308). Such updating may be performed on a periodic or repetitive basis. The announcement timing control module 222 may then access the one or more factors (operation 304) to determine once again whether a new announcement frequency is warranted (operation 306), continuing in such a manner indefinitely.

While the operations 302-308 of the method 300 of FIG. 2 are illustrated in a particular order of performance, other orders for the operations 302-308, including simultaneous, concurrent, and/or overlapping of multiple operations 302-308 are possible. For example, the accessing of the one or more factors (operation 304) may occur on a more-or-less continual or repetitive basis, while the determining of the announcement frequency based on those factors may occur concurrently, but less often.

Implantable medical devices serving as the electronic device 200 of FIG. 1 will thus be described in conjunction with FIGS. 3A-B and 4A-B, in which the features included in various embodiments described hereafter could be implemented. However, numerous variations of such a device exist in which various circuits and methods discussed below can be implemented.

Figure 3A:
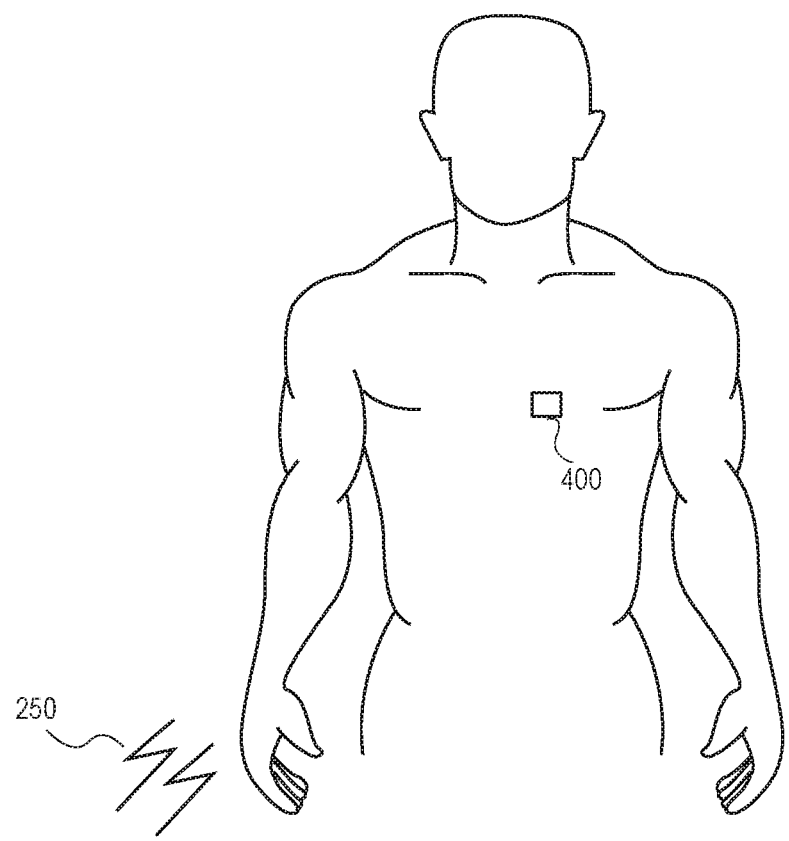
FIG. 3A illustrates a system for the detection of environmental conditions in communication with an external device through a wireless communication connection.
Figure 3A:
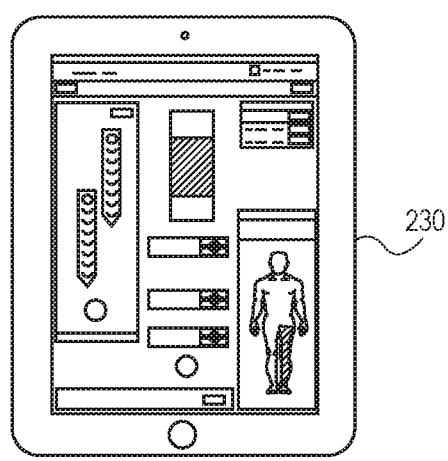

FIG. 3A illustrates a monitoring device 400, which may be implanted or external to the patient, and may dynamically communicate with an external device 230 using one or more wireless communication connections 250. In certain embodiments, monitoring device 400 is a device capable of recording heart electrical activity such as an EGM-based monitor. In certain embodiments, monitoring device 400 is a subcutaneous EGM-based monitor, such as an implantable loop recorder (ILR) (e.g., an implantable cardiac monitor (ICM) or a subcutaneous atrial fibrillation (AF) monitor). In certain embodiments, the ILR is subcutaneously (i.e., just under the skin) implanted in the chest of a patient to the left of the breastbone. An ILR may include two or more electrodes attached to the casing or electrically connected to the device and spaced sufficiently far apart that cardiac events are sensed. An ILR that may be used with the invention is, e.g., a SJM Confirm™ Implantable Cardiac Monitor of St. Jude Medical. Examples of ILRs that may be used with the invention are described in U.S. Pat. No. 8,241,221 (Park), U.S. Pat. No. 8,467,864 (Park), and U.S. Pat. No. 7,294,108 (Bomzin et al.), each of which is incorporated herein by reference in its entirety.

An ILR may begin recording heart electrical activity in response to, for example, the ILR detecting electrical activity indicative of a heart-related problem, such as atrial fibrillation (AF), atrial tachycardia, ventricular tachycardia, asystole, syncope, and so on. In other examples, the ILR may begin such recording in response to receiving a signal from a patient-triggered external activator serving as the external device 230. Consequently, ILR operation may benefit from a dynamic increase in the announcement frequency to more quickly create a wireless communication connection 250 between the activator and the ILR to allow the ILR to receive the signal from the activator based on one or more of the factors described herein, such as detection of an elevated heart rate, an arrhythmia, an increased or decreased level of patient physical activity, change in posture, time of day and/or the like. As a result, the connection 250 may be established during times associated with a higher probability of the patient being symptomatic, and thus at times during which the signal from the activator is more likely to be received.

In certain embodiments, monitoring device 400 is also a cardiac stimulation device, such as a subcutaneous implantable cardioverter defibrillator (S-ICD) or a leadless pacemaker. An S-ICD may include multiple subcutaneous extracardiac electrodes (also referred to as remote sensing electrodes) for detecting electrical cardiac signals within the chest of the patient. The subcutaneous extracardiac electrodes are preferably extravascular and can be, e.g., paddle electrodes or coil electrodes mounted subcutaneously outside of the rib cage, but are not limited thereto. Exemplary locations of the subcutaneous extracardiac electrodes include near the bottom of the sternum (slightly to the left), below the left pectoral area, and below the clavicle and on the back left side (just below the shoulder blade). Of course, additional and/or alternative locations for subcutaneous electrodes are within the scope of the present invention.

Examples of S-ICDs that may be used with the invention are described in U.S. Pat. No. 7,970,473 (Nabutovsky, et al.), U.S. Pub. No. 2016/0030757 (Jacobson et al.), and U.S. Pat. No. 9,320,448 (Xi et al.), each of which is incorporated herein by reference in its entirety. Examples of leadless pacemakers that may be used with the invention are described in U.S. Pat. No. 9,278,218 (Karst et al.), U.S. Pat. No. 9,227,077 (Jacobson et al.) and U.S. Pat. No. 8,798,745 (Jacobson et al.), each of which is incorporated herein by reference in its entirety.

In certain embodiments, multiple monitoring devices 400 are used in conjunction with one another in a system and may communicate through conductive communication, RF, or other wireless communication. In certain embodiments, one of the monitoring devices 400 of a system of monitoring devices 400 is designated as a master device that gathers and, in some embodiments, processes communications from slave monitoring devices 400 and communicates with an external device 230 using one or more wireless communication connections 250. For example, a master monitoring devices 400 may be a S-ICD that communicates with a slave monitoring device 400, such as a leadless pacemaker, through conductive communication, as described in, e.g., U.S. Pub. No. 2016/0030757 (Jacobson et al.), incorporated herein by reference. The S-ICD may communicate with an external device 230 using a Bluetooth® interface or another wireless communication interface implementing some wireless communication protocol or standard.

Figure 3B:
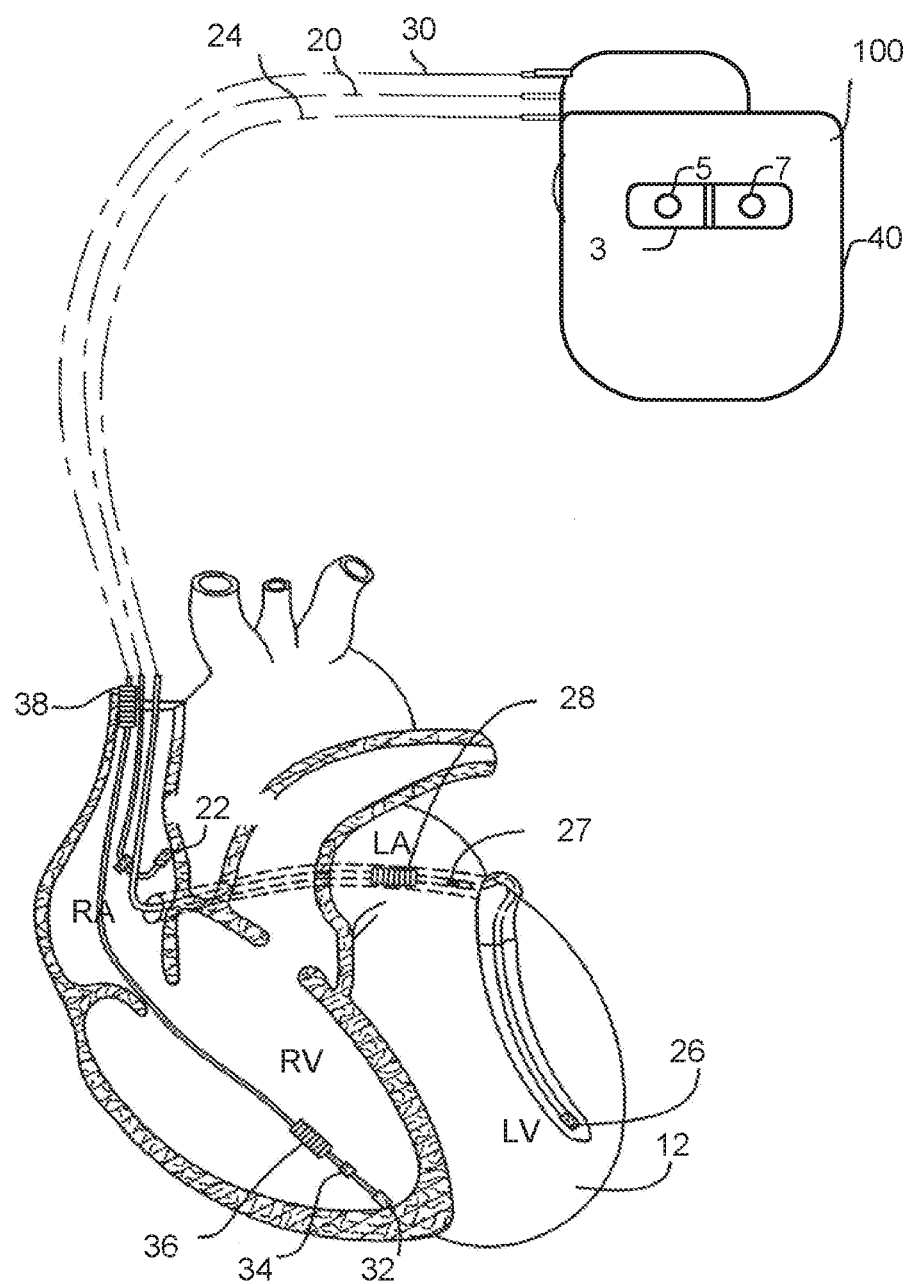
FIG. 3B is a partly cut-away view of an example implantable cardiac stimulation device in electrical communication with at least three leads implanted into a patient's heart for delivering multi-chamber stimulation and shock therapy and for detecting environmental conditions.

FIG. 3B illustrates an implantable cardiac stimulation device 100 in electrical communication with a patient's heart 12 by way of three leads 20, 24, and 30 suitable for delivering multi-chamber stimulation and/or shock therapy. To sense atrial cardiac signals and to provide right atrial chamber stimulation therapy, the device 100 may be coupled to an implantable right atrial lead 20 including at least one right atrial tip electrode 22 that may be implanted in the patient's right atrial appendage. The right atrial lead 20 may also include a right atrial ring electrode to allow bipolar stimulation or sensing in combination with the atrial tip electrode 22.

To sense the left atrial and left ventricular cardiac signals and to provide left-chamber stimulation therapy, the stimulation device 100 may be coupled to a "coronary sinus" lead 24 designed for placement in the "coronary sinus region" via the coronary sinus ostium in order to place a distal electrode adjacent to the left ventricle and additional one or more electrodes adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 may be designed to receive atrial and/or ventricular cardiac signals, deliver left ventricular pacing therapy using at least one left ventricular tip electrode 26 for unipolar configurations or in combination with a left ventricular ring electrode for bipolar configurations, and/or deliver left atrial pacing therapy using at least one left atrial ring electrode 27 as well as shocking therapy using at least one left atrial coil electrode 28.

The stimulation device 100 of FIG. 3B may also be in electrical communication with the patient's heart 12 by way of an implantable right ventricular lead 30 including, in this embodiment, a right ventricular (RV) tip electrode 32, a right ventricular ring electrode 34, a right ventricular coil electrode 36, a superior vena cava (SVC) coil electrode 38, and/or so on. The right ventricular lead 30 may be inserted transvenously into the heart 12 so as to place the right ventricular tip electrode 32 in the right ventricular apex such that the right ventricular coil electrode 36 is positioned in the right ventricle and the SVC coil electrode 38 will be positioned in the right atrium and/or superior vena cava.

Accordingly, the right ventricular lead 30 may be capable of receiving cardiac signals, and delivering stimulation in the form of pacing and shock therapy to the right ventricle.

In certain embodiments, the implantable stimulation device 100 may incorporate one or more optical sensors 3 (also referred to as photoplethysmography (PPG) sensors) integrated with or attached to its housing 40.

Optical sensors 3 may also be integrated with or attached to a monitoring device 400 (FIG. 3A) implanted in the pectoral region of a patient. In certain embodiments, optical sensor 3 may be used to detect patient interaction (as discussed in detail below). In certain embodiments, optical sensor 3 may be used to determine a person's heart activity, and these measurements may be used in lieu of, or in conjunction with, electrical activity measurements. Changes in the optical signal over time can be used to determine heart activity, even if the position of the optical sensor is far removed from the heart. In some embodiments, the monitoring device 400 may include both an optical sensor and an EGM-based monitor. Optical sensors that may be used with the current disclosure are disclosed in U.S. Pat. No. 8,328,728 (Schecter), U.S. Pat. No. 8,478,403 (Wenzel et al.), and U.S. Pat. No. 9,022,945 (Fayram et al.), each of which is incorporated herein in its entirety. In other embodiments, the monitoring device 400 may include an EGM-based monitor and an impedance measurement circuit. Impedance measurement circuits that may be used with the current disclosure are disclosed in U.S. Pat. No. 8,065,005 (Wong et al.) and U.S. Pat. No. 9,265,436 (Min, et al.), each of which is incorporated herein in its entirety.

The optical sensor, which can be used to obtain a PPG signal, includes a light source and a light detector. The light source 5 can include, e.g., at least one light-emitting diode (LED), laser, incandescent lamp or laser diode, but is not limited thereto. The light detector 7 can include, e.g., at least one photoresistor, photodiode, phototransistor, photodarlington or avalanche photodiode, but is not limited thereto. Light detectors are often also referred to as photodetectors or photocells.

The light source 5 outputs light that is reflected, absorbed and/or scattered by surrounding patient tissue, and reflected/scattered light is received by the light detector 7. In this manner, changes in reflected light intensity are detected by the light detector 7, which outputs a signal indicative of the changes in detected light. The output of the light detector 7 can be filtered and amplified. The signal can also be converted to a digital signal using an analog to digital converter, if the PPG signal is to be analyzed in the digital domain. A PPG sensor can use a single wavelength of light, multiple discrete wavelengths, or a broad spectrum of many wavelengths. If multiple wavelengths are used, the timing of the signals may be multiplexed to determine optical response of tissue at different wavelengths. Additional details of exemplary implantable PPG sensors that may be used in accordance with the present disclosure are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

Exemplary details of how to attach a sensor module to an electronic device 200 are described in U.S. Pat. No. 7,653,434, entitled "Autonomous Sensor Modules for Patient Monitoring" (Turcott et al.), which is incorporated herein by reference. It is also possible that the optical sensor 3 be integrally part of the implantable stimulation device 100 or a monitoring device 400. For example, the optical sensor 3 can be located within the housing 40 of an electronic device 200 that has a window through which light can be transmitted and detected. In a specific embodiment, the optical sensor 3 has a titanium frame with a light transparent quartz or sapphire window that can be welded into a corresponding slot cut in the housing of the implantable stimulation device 100 or monitoring device 400. This will insure that the electronic device 200 enclosure with the welded optical sensor will maintain a hermetic condition.

Where the optical sensor is incorporated into or attached to an implanted electronic device, the light source and the light detector can be mounted adjacent to one another on the housing or header of the electronic device, or on the bottom of the device, or at any other location. The light source and the light detector can be placed on the side of an electronic device that, following implantation, faces the chest wall, and are configured such that light cannot pass directly from the source to the detector. The placement on the side of the electronic device that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source and the light detector can be placed on the face of the electronic device that faces the skin of the patient. The light source and light detector may be positioned to face each other at a distance apart. Other variations are also possible.

Figure 4A:
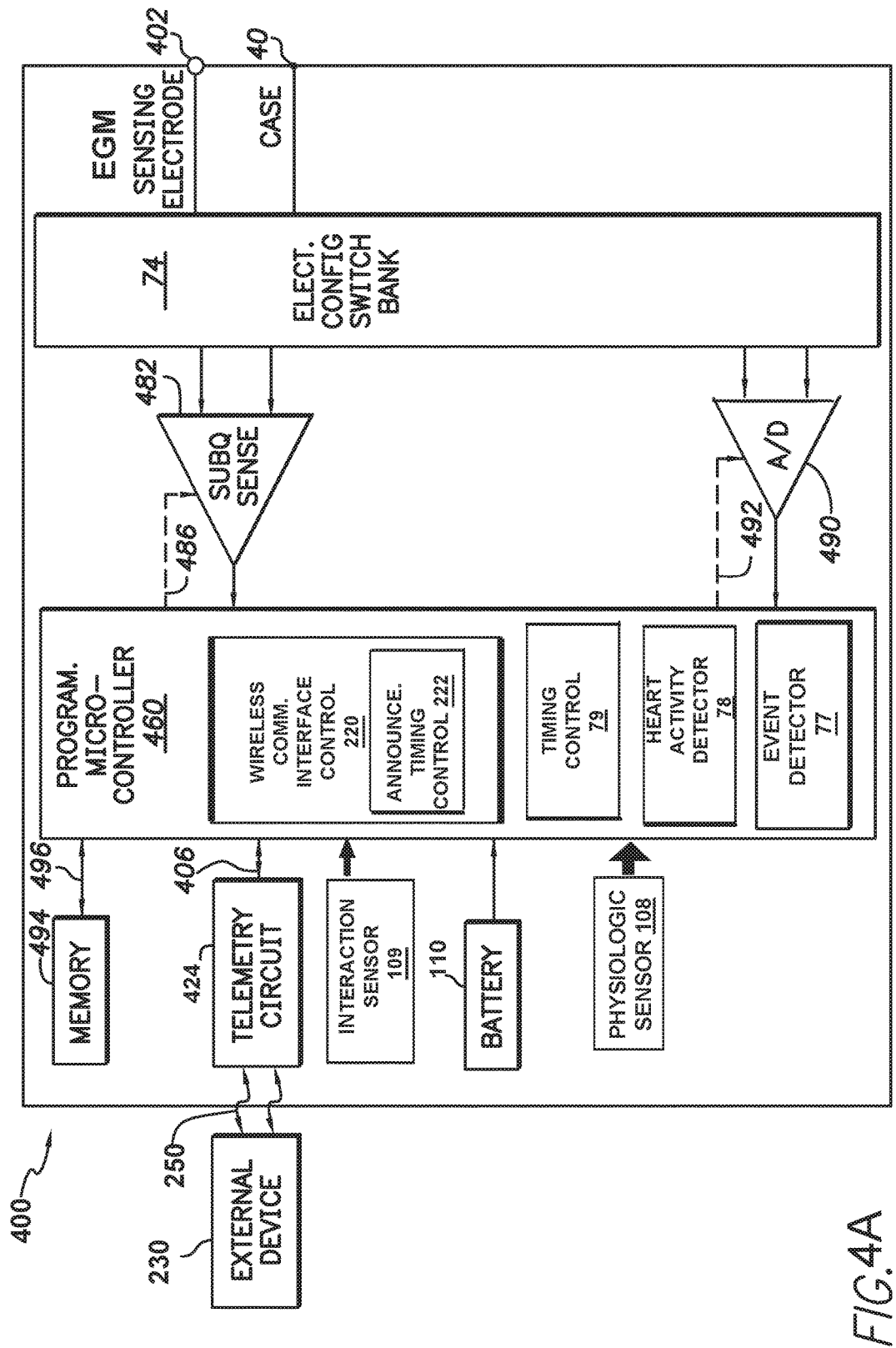
FIG. 4A is a functional block diagram of selected components of a subcutaneous implantable monitor of 3A, including an announcement timing control module for dynamic announcing for creation of wireless communication connections.

FIG. 4A is a functional block diagram of selected components of a monitoring device 400. The particular monitoring device 400 shown in FIG. 4A is for illustration purposes only, and one of ordinary skill in the pertinent art could readily duplicate, eliminate, or disable the appropriate circuitry in any desired combination to provide an ECG or EGM-based monitor.

Housing 40 (shown schematically) of monitoring device 400 includes a connector having one or more EGM sensor terminals 402 adapted for connection to subcutaneous (SubQ) EGM sensors mounted to (or connected to) the exterior housing of the device. Housing 40 (often referred to as the "can", "case" or "case electrode") can also act as the return (common) electrode, or anode, for any sensing electrodes implanted separately from the device. Only one EGM sensing electrode terminal is shown, but additional terminals can be provided to accommodate additional sensing electrodes or sensing leads.

At the core of monitoring device 400 is a programmable microcontroller 460, which controls heart activity detection, such as heart rate, morphology, heart rate variability, and arrhythmia, and event detection, such as myocardial infarctions, strokes, cardiac ischemia, and pain (whether due to angina or another underlying condition being monitored and/or treated by the monitoring device 400 or another device in a system). The microcontroller 460 includes a microprocessor, or equivalent control circuitry, designed specifically for detecting heart activity and/or events and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions is well known in the art.

A switch bank 74 includes a plurality of switches for switchably connecting the EGM electrodes (assuming there is more than one) to the appropriate I/O circuits, thereby providing complete electrode programmability. A sense amplifier 482 is coupled to the EGM electrodes through switch bank 74 for sensing electrical cardiac activity. Sense amplifier 482 is capable of sensing signals in accordance with otherwise conventional techniques. The switch bank 74 determines the "sensing polarity" of the cardiac signal by selectively closing the appropriate switches, as is also known in the art. In this way, the clinician may program the sensing polarity. Sense amplifier 482 preferably employs a low power, precision amplifier with programmable gain and/or automatic gain control and/or automatic sensitivity control, bandpass filtering, and a threshold detection circuit, known in the art, to selectively sense electrical signals of interest. The automatic gain control, if implemented, enables the monitoring device 400 to deal effectively with the difficult problem of sensing any low frequency, low amplitude signal characteristics. The gain control is actuated by the programmable microcontroller 460. The gains are controlled on sense amplifier 482 by the microcontroller using control line 486. The outputs of the sense amplifier are connected to microcontroller 460.

EGM signals and other sensed signals are also applied to the inputs of an analog to digital (A/D) data acquisition system 490. The gain of the A/D converter 490 is controlled by the microprocessor 460 by signals along control line 492 in order to match the signal amplitude and/or the resolution to a range appropriate for the function of the A/D converter 490. The data acquisition system 490 is configured to acquire EGM signals, convert the raw analog data into a digital signal, and store the digital signals for later processing and/or telemetric transmission to an external device 230. The data acquisition system 490 is coupled to the EGM electrode 402 through switch bank 74 to sample cardiac signals. The microcontroller 460 is further coupled to a memory 494 by a suitable data/address bus 496, wherein the programmable operating parameters used by the microcontroller 460 are stored and modified, as required, in order to customize the operation of monitoring device 400 to suit the needs of a particular patient. Such operating parameters define, for example, the particular parameters to be used to detect stroke or AF.

EGM-based heart activity detector unit 78 detects cardiac rhythm, including heart rate and heart variability, and cardiac morphology. The disclosure utilizes the sense amplifier 482 to sense electrical signals to determine whether a cardiac rhythm is physiologic or pathologic. As used herein, "sensing" is reserved for the noting of an electrical depolarization, and "detection" is the processing of sequential sensed depolarization signals potentially in conjunction with the sensor input to establish a diagnosis of an arrhythmia. The timing intervals between sensed events (e.g., P-P intervals or R-R intervals) are detected by a timing control unit 79 of microcontroller 460 and then classified by an EGM-based heart activity detector unit 78 by, for example, comparing the intervals to predefined rate zone limits indicative of, e.g., a tachycardia, bradycardia, AF, or asystole episode. Techniques for determining arrhythmias in an implantable device are described, for example, in U.S. Pat. No. 9,295,852 (Williamson), which is incorporated herein by reference. Techniques for measuring and quantifying HRV are described, for example, in U.S. Patent Pub. No. 20110066055 (Bharmi et al.), incorporated herein by reference. HRV is a measure of the variation in heart rate over time. Briefly, in one example described therein, HRV is assessed based on an analysis of R-R intervals, including various frequency components thereof.

Event detector unit 77 may use the output of heart activity detector unit 78 and/or cardiac signals from an analog to digital (A/D) data acquisition system 490 to detect events, such as myocardial infarctions, cardiac ischemia, strokes, and pain. For example, HRV can be reduced by both stroke and cardiac ischemia. However, reductions in HRV may be more pronounced from stroke than when cardiac ischemia occurs and hence HRV can be used to discriminate stroke from cardiac ischemia, at least within some patients. One possible reason for this difference is that the efferent neural pathways involved in heart rate control are affected by stroke, but not necessarily from a site of cardiac ischemia. For a discussion of the effects of stroke on HRV see, for example, Tokgozoglu at al. "Effects of Stroke Localization on Cardiac Autonomic Balance and Sudden Death" Stroke 1999, 30, 1307-1311, incorporated herein by reference.

U.S. Pat. No. 8,241,221 (Park), incorporated herein by reference in its entirety, describes techniques that may be used in accordance with the present disclosure for detecting stroke within a patient using a subcutaneous monitor based on an analysis of features of an electrogram (EGM) sensed within the patient. Exemplary EGM features indicative of possible stroke include the onset of prominent U-waves, the onset of notched T-waves, and changes in ST segment duration or QT duration or dynamic trends in these parameters. ST segment variations may be caused by abnormalities in the polarizations of cardiac tissue during an acute myocardial infraction. ST segment variations may arise because of differences in the electric potential between cells that have become ischemic and those cells that are still receiving normal blood flow. ST segment variations may be an indication of injury to cardiac muscle, changes in the synchronization of ventricular muscle depolarization, drug or electrolyte influences, or the like.

U.S. Pat. No. 8,469,897 (Toren-Herrinton, et al.), incorporated herein by reference in its entirety, describes techniques that may be used in accordance with the present disclosure for determining the onset and determination of an ischemic or AMI condition based on a ST segment deviation. The cardiac cycle is composed of a P-wave, a Q-wave, an R-wave, an S-wave, and a T-wave. The portion of the signal between the S-wave and T-wave constitutes a ST segment. The ST segment may have a voltage level that aligns with the voltage level of a baseline heart rhythm. Alternatively, the ST segment may have a voltage level that is shifted above or shifted below the baseline. ST segment variations indicate a potential coronary episode. ST segment variations may include ST deviations or ST shifts. A ST deviation is determined by subtracting an average PQ segment (e.g., the isoelectric segment) voltage from the ST segment voltage for a heartbeat. The ST deviation provides a measure of the change in variability over a period of time. A ST shift is determined by changes in the ST deviation over a period of time. For example, a current ST shift may be calculated by subtracting a stored baseline ST deviation from a newly acquired ST deviation. ST deviations and ST shifts may be calculated as averages over multiple cardiac cycles as well.

The discrimination of ischemia related and non-ischemia related shifts in the ST segment may be determined by the event detector 77 by using a statistical determination of the variability of the ST segment shift. For example, a plurality of ST segment shifts may be collected to obtain a ST threshold. Then the ST threshold is used in a comparison with subsequently measured ST segment shifts to identify the onset of a coronary episode. When the measured ST segment shift is less than a ST threshold, the termination of the coronary episode may be identified. Upon detecting the onset of a coronary episode, either an ischemic event or an AMI event, the cardiac signals are stored in memory 494.

One or more physiologic sensors 108 may be mounted on or within monitoring device 400 or otherwise in communication with monitoring device 400. Event detector unit 77 may base the detection of events on the output of one or physiologic sensors 108. Various physiologic sensors that can be used in conjunction with the current invention are discussed in: U.S. patent application Ser. No. 11/856,443, of Zhao, filed Sep. 17, 2007, entitled "MEMS-Based Left Atrial Pressure Sensor for use with an Implantable Medical Device" and in U.S. patent application Ser. No. 11/623,663, filed Jan. 16, 2007, of Zou et al., entitled "Sensor/Lead Systems for use with Implantable Medical Devices," each of which is incorporated herein by reference in its entirety. Physiological sensors 108 may be one or more motion sensors, acceleration sensors such as an accelerometer, gyroscope, temperature sensors, minute ventilation sensors, posture sensors, impedance sensors, optical sensors, oxygen saturation sensors, and the like. The following patents, each of which is incorporated herein by reference in its entirety, describe exemplary activity sensors that may be used as a physiologic sensor 108: U.S. Pat. No. 6,658,292 to Kroll et al., entitled "Detection of Patient's Position and Activity Status using 3D Accelerometer-Based Position Sensor"; U.S. Pat. No. 6,625,493 (Kroll et al.), entitled "Orientation of Patient's Position Sensor using External Field"; U.S. Pat. No. 6,466,821 (Pianca et al.), entitled "AC/DC Multi-Axis Accelerometer for Determining Patient Activity and Body Position;" U.S. Pub. No. 20150265839, entitled "Temperature Sensor for a Leadless Cardiac Pacemaker." An impedance sensor may be used to measure alterations of impedance through the chest cavity to determine changes in breathing. Respiration sensors such as impedance sensors may be used to monitor exertion and shortness of breath, which may be used by event detector unit 77 in conjunction with cardiac signals from A/D 490, as an indicator of a myocardial infraction. In certain embodiments, patient posture data is determined from sensed EGM data, as described in U.S. Pat. No. 7,636,599 (Koh et al.).

One or more interaction sensors 109 (discussed in further detail below) may be mounted on or within monitoring device 400 or otherwise in communication with monitoring device 400, in order to permit a user, such as the patient or a family member, to trigger a wireless communication connection 250 between monitoring device 400 and an external device 230. In certain embodiments, interaction sensors 109 may also be used to trigger activation of EGM storage.

The operating parameters of implantable monitoring device 400 may be non-invasively programmed into the memory 494 through telemetry circuit 424 in telemetric communication with external device 230 or other external device, such as a programmer, transtelephonic transceiver, or a diagnostic system analyzer. The telemetry circuit 424 is activated by the microcontroller 460 by a control signal 406. The telemetry circuit 424 advantageously allows SubQ EGM electrograms and status information relating to the operation of monitoring device 400 (as contained in the microcontroller 460 or memory 494) to be sent to external device 230 through an established communication link 250, and then on to a centralized processing system, where appropriate. The telemetry circuit 424 also allows an implantable monitoring device 400 to include a patient-triggered activation option for EGM storage. The telemetry circuit 424 permits communication between monitoring device 400 and external physiologic sensor(s) 108 located in other location(s) and/or other devices (e.g., drug pumps or patient worn/carried electronic devices or sensors).

The implantable monitor additionally includes a battery 110 that provides operating power to all of the circuits shown in FIG. 4A. The battery is capable of operating at low current drains for long periods of time for monitoring. The battery 110 also should have a predictable discharge characteristic so that elective replacement time can be detected.

In accordance with various embodiments disclosed below, the microcontroller 460 may also include a wireless communication control module 220, which may operate as the wireless communication control module 220 of FIG. 1.

Moreover, the wireless communication control module 220 may include an announcement timing control module 222 serving as the announcement timing control module 222 of FIG. 1. In such examples, the telemetry circuit 424 may be operated as the wireless communication interface 210 of FIG. 1, such as a Bluetooth® interface or another wireless communication interface implementing some wireless communication protocol or standard. In some embodiments, the announcement timing control module 222 may receive information from the subcutaneous sensing circuit 482, the data acquisition system 490 (e.g., when an arrhythmia occurs), and/or the like, as well as other information available within the monitoring device 400, either directly or via stored data in the memory 494, to determine a desired announcement frequency.

In addition to or in conjunction with increasing frequency of announcements, monitoring device 400 may also issue a patient alert when an event or potential event, such as acute myocardial infarction or stroke, is detected. The patient alert may direct external device 230 to call an emergency number, such as 911. The alert may also instruct the patient and/or caregiver to move within the external device's 230 connection range. The alert may also prompt the external device 230 to provide instructions to the user to, e.g., call 911 or their healthcare provider and/or provide a questionnaire (e.g., through an app) to confirm a detected event.

The microcontroller 460, in one embodiment, may perform the functions of the heart activity detector 78, event detector 77, the timing control 79, the wireless communication control module 220, and/or other functions described herein by executing instructions stored in the memory 494. Accordingly, the microcontroller 460 may operate as the heart activity detector 78 for periods of time, the event detector 77 for periods of time, the timing control 79 for other periods of time, and so on. In some examples, the microcontroller 460 may operate as these particular functional blocks in a concurrent or parallel manner.

In certain embodiments, an electronic device 200, e.g., monitoring device 400 (FIG. 4A) or implantable stimulation device 100 (FIG. 4B), may include a neuromodulation implantable pulse generator (IPG) and a neuro stimulation pulse generator circuit to generate stimulation pulses for a brain or spinal cord nervous system, such as those used for spinal cord stimulation (SCS) or deep brain stimulation (DBS). The stimulation pulses may be delivered by a plurality of electrodes through a neuro output lead. The neuro stimulation pulse generator circuit may be controlled by a microcontroller via appropriate control signals to trigger or generate the stimulation pulses. Examples of EPGs that may be used with the current invention are disclosed in U.S. Pat. Nos. 9,288,614 and 8,983,604 (Keel et al.), each of which is incorporated herein by reference in its entirety. For example, Keel et al. describe a neurostimulation system, which may be an SCS system, having a lead with various electrodes for implant within an epidural space of an upper thoracic region of the patient. The SCS device is equipped to sense both neural electrical signals and far-field cardiac electrical signals and to discriminate therebetween. In one specific example, the SCS device has a cardiac sense amplifier and a separate neural sense amplifier. In an example where a single wideband sense amplifier is instead provided, the SCS device selectively filters a frequency spectrum sensed by the wide-band amplifier to separate cardiac signals from neural signals. Still further, the SCS device may identify and distinguish various cardiac events such as atrial depolarization events (P-waves); ventricular depolarization events (R-waves); and ventricular repolarization events (T-waves) using one or more sensing vectors, i.e. a particular combination of electrodes with which signals are sensed. Different cardiac events can be distinguished based, for example, on signal amplitude, signal slope, signal morphology, sensing vector or sensing electrode spacing. For example, a vector spanning the atria of the heart will more readily sense P-waves; whereas a vector remote from the atria will typically not sense P-waves and so a comparison of far-field signals derived from those different vectors may be used to discriminate P-waves from R-waves. The relative spacing of electrode pairs can also provide a basis for distinguishing R-waves from P-waves, with relatively wider inter-electrode spacing providing signals that emphasize R-waves as opposed to P-waves. That is, the device may be equipped to record or obtain cardiac signals from a different electrode configuration (i.e. "vector") than used for the neural sensing electrode configuration to help distinguish cardiac signals from neural signals. For example, for an Octrode™ lead, the distal electrode to "Can" is a relatively large field vector that picks up the R-wave; whereas the distal to "Ring 8" is a narrower field vector that picks up atrial activity. An Octrode™ lead is a type of linear eight electrode percutaneous lead provided by St Jude Medical™.

An electronic device 200, including monitoring device 400 and implantable stimulation device 100 and may uses P-waves, R-waves and other features of the cardiac signal to detect heart rate variability (HRV), atrial and ventricular arrhythmias, prolonged QT intervals, ST segment shifts or deviations, ischemia or other cardiac conditions or parameters. Insofar as HRV is concerned, the device may detect: high frequency (HF) components of HRV; low frequency (LF) components of HRV; and very low frequency (VLF) components of HRV, as well as a pNN50 statistical value.

The electronic device 200 device may detect myocardial infarctions based on shifts or deviations in ST segments. An elevation of ST segments may be used as an indicator of potentially life-threatening acute myocardial infarction requiring immediate intervention. An ST segment depression may be used as an indicator that the patient has partially occluded arteries, requiring monitoring and possibly therapeutic interventions, such as medication. The electronic device 200 may detect pain based on a combination of elevated heart rate and patient movement associated with pain.

Figure 4B:
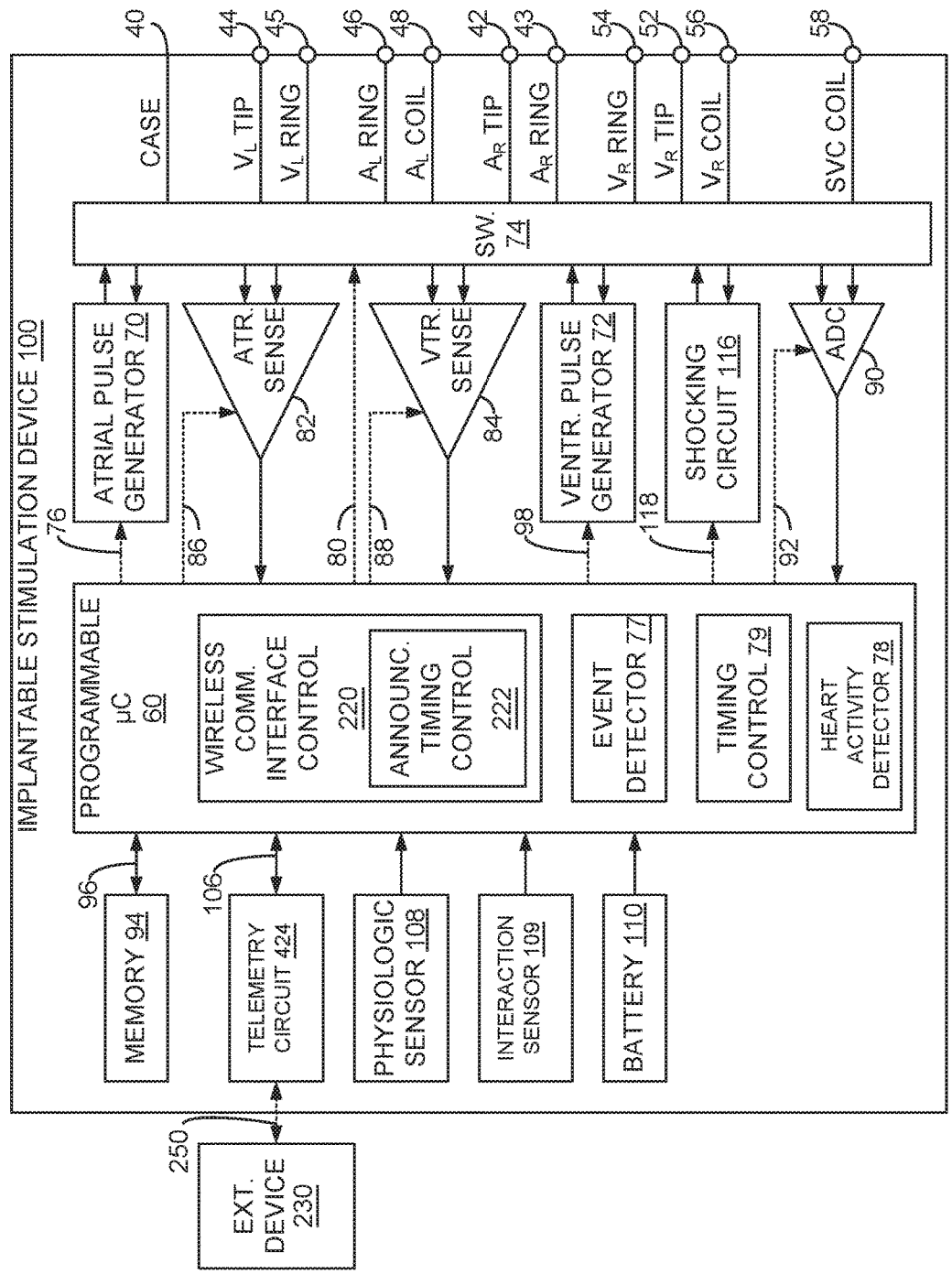
FIG. 4B is a functional block diagram of the example implantable cardiac stimulation device of FIG. 3B, illustrating the basic elements providing pacing stimulation, cardioversion, and defibrillation in four chambers of the heart via one or more pulse generators, as well as an announcement timing control module for dynamic announcing for creation of wireless communication connections.

FIG. 4B illustrates a simplified block diagram of the multi-chamber implantable cardiac stimulation device 100, which may be capable of treating both fast arrhythmia and slow arrhythmia with stimulation therapy, including cardioversion, defibrillation, and pacing stimulation. The particular multi-chamber device 100 shown in FIG. 4B is for illustration purposes only, and one of ordinary skill in the pertinent art could readily duplicate, eliminate, or disable the appropriate circuitry in any desired combination to provide a device capable of treating the appropriate one or more chambers with cardioversion, defibrillation, and/or pacing stimulation.

The stimulation device 100 may include a housing 40 which is often referred to as a "can," "case," or "case electrode," and which may be programmably selected to act as the return electrode for all "unipolar" modes. The housing 40 may further be used as a return electrode alone or in combination with one or more of the coil electrodes 28, 36, or 38 (FIG. 3B), for defibrillation shocking purposes. The housing 40 may further include a connector having a plurality of terminals 42, 43, 44, 45, 46, 48, 52, 54, 56, and 58 (shown schematically and, for convenience, the names of the electrodes to which they are connected are shown next to corresponding terminals). As such, in order to achieve right atrial sensing and stimulation, the connector may include at least one right atrial tip terminal ($A_R$ TIP) 42 adapted for connection to the atrial tip electrode 22. The connector may also include a right atrial ring terminal ($A_R$ RING) 43 for connection to the right atrial ring electrode.

To achieve left chamber sensing, pacing, and/or shocking, such a connector may include a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, that are adapted for connection to the left ventricular tip electrode 26, a left ventricular ring electrode (not shown), the left atrial ring electrode 27, and the left atrial coil electrode 28, respectively (FIG. 3B).

To support right ventricular sensing, pacing, and/or shocking, the connector may further include a right ventricular tip terminal ($V_R$ TIP) 52, a right ventricular ring terminal ($V_R$ RING) 54, a right ventricular shocking coil terminal ($R_V$ COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

At the core of the stimulation device 100 is a programmable microcontroller 60 that may control the various modes of stimulation therapy. The microcontroller 60 may include a microprocessor or equivalent control circuitry designed specifically for controlling the delivery of stimulation therapy, and may include random access memory (RAM) and/or read-only memory (ROM), logic and timing circuitry, state machine circuitry, and/or input/output (I/O) circuitry. Further, the microcontroller 60 may have the ability to process or monitor various input signals (data) as controlled by a program code stored in a designated block of memory. Exemplary types of control circuitry that may be used with the invention include the microprocessor-based control system of U.S. Pat. No. 4,940,052 (Mann et. al.) and the state-machines of U.S. Pat. No. 4,712,555 (Thornander et al.) and U.S. Pat. No. 4,944,298 (Sholder), each of which is incorporated herein by reference in its entirety.

In the embodiment of FIG. 4B, the stimulation device 100 includes an atrial pulse generator 70 and a ventricular pulse generator 72 that may generate stimulation pulses for delivery by the right atrial lead 20, the right ventricular lead 30, and/or the coronary sinus lead 24 via an electrically configurable switch 74. To provide the stimulation therapy in each of the four chambers of the heart 12, the atrial pulse generator 70 and the ventricular pulse generator 72 may include, for example, dedicated pulse generators, independent pulse generators, multiplexed pulse generators, and/or shared pulse generators. The atrial pulse generator 70 and the ventricular pulse generator 72 may be generally controlled by the microcontroller 60 via appropriate control signals 76 and 98, respectively, to trigger or inhibit the stimulation pulses.

The microcontroller 60 may further include timing control circuitry 79, which may be used to control timing of the stimulation pulses such as, for example, pacing rate, atrioventricular (AV) delay, atrial interchamber (A-A) delay, and/or ventricular interchamber (V-V) delay. Such timing control circuitry 79 may also be used to keep track of the timing of refractory periods, noise detection windows, evoked response windows, alert intervals, marker channel timing, and so on.

The switch 74 may include a plurality of switches for connecting the desired electrodes to the appropriate I/O circuits, thereby providing complete electrode programmability. Accordingly, the switch 74, in response to a control signal 80 from the microcontroller 60, may determine the polarity of the stimulation pulses (e.g., unipolar, bipolar, cross-chamber, and the like) by selectively opening and closing the appropriate combination of switches. Atrial sensing circuits 82 and ventricular sensing circuits 84 may also be selectively coupled to the right atrial lead 20, coronary sinus lead 24, and the right ventricular lead 30 through the switch 74 for detecting the presence of cardiac activity in each of the four chambers of the heart 12.

Accordingly, the atrial sensing circuit 82 and the ventricular sensing circuit 84 may include dedicated sense amplifiers, multiplexed amplifiers, and/or shared amplifiers. The switch 74 determines the "sensing polarity" of the cardiac signal by selectively closing the appropriate switches of the switch 74. In this way, the clinician may program the sensing polarity independent of the stimulation polarity.

Each of the atrial and ventricular sensing circuits 82, 84 may employ one or more low-power precision amplifiers with programmable gain, automatic gain, and/or sensitivity control, one or more band-pass filters, and/or a threshold detection circuit, to selectively sense the cardiac signal of interest. The automatic sensitivity control may enable the stimulation device 100 to deal effectively with the difficult problem of sensing the low amplitude signal characteristics of atrial or ventricular fibrillation.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion in response to the absence or presence of cardiac activity, respectively, in the appropriate chambers of the heart 12. The atrial and ventricular sensing circuits 82 and 84, in turn, may receive control signals over signal lines 86 and 88 from the microcontroller 60 for controlling the gain, threshold, polarization charge removal circuitry, and the timing of any blocking circuitry coupled to the inputs of the atrial and ventricular sensing circuits 82 and 84.

For arrhythmia detection, the stimulation device 100 may include a heart activity detector 78 that utilizes the atrial and ventricular sensing circuits 82 and 84 to sense cardiac signals for determining whether a rhythm may be physiologic or pathologic. As used herein, "sensing" generally refers to the process of noting an electrical signal, while "detection" generally refers to the step of confirming the sensed electrical signal as the signal being sought by the detector. As an example, "detection" applies to the detection of both proper rhythms (i.e., "P wave" or "R wave") as well as improper dysrhythmias including arrhythmia and bradycardia (e.g., detection of the absence of a proper rhythm).

The timing intervals between sensed events (e.g., P-waves, R-waves, and/or depolarization signals associated with fibrillation which are sometimes referred to as "F-waves" or "Fib-waves") may then be classified by the heart activity detector 78 by comparing them to a predefined rate zone limit (e.g., bradycardia, normal, low-rate ventricular tachycardia, high-rate ventricular tachycardia, fibrillation rate zones, and so on) and various other characteristics (e.g., sudden onset, stability, morphology, information from one or more physiologic sensors 108, and so on) to determine the type of remedial therapy required (e.g., bradycardia pacing, anti-tachycardia stimulation, cardioversion shocks, and/or defibrillation shocks, collectively referred to as "tiered therapy").

Physiologic sensors 108 may be mounted on a lead or mounted on or within stimulation device 100 or otherwise in communication with stimulation device 100. Various physiologic sensors that can be used in conjunction with the current invention are discussed in: U.S. patent application Ser. No. 11/856,443, of Zhao, filed Sep. 17, 2007, entitled "MEMS-Based Left Atrial Pressure Sensor for use with an Implantable Medical Device" and in U.S. patent application Ser. No. 11/623,663, filed Jan. 16, 2007, of Zou et al., entitled "Sensor/Lead Systems for use with Implantable Medical Devices," each of which is incorporated herein by reference in its entirety. Physiological sensors 108 may be one or more motion sensors, accelerometers, gyroscopes, temperature sensors, minute ventilation sensors, posture sensors, impedance sensors, optical sensors, oxygen saturation sensors, and the like. The following patents, each of which is incorporated herein by reference in its entirety, describe exemplary activity sensors that can be used to determine patient activity: U.S. Pat. No. 6,658,292 to Kroll et al., entitled "Detection of Patient's Position and Activity Status using 3D Accelerometer-Based Position Sensor"; U.S. Pat. No. 6,625,493 to Kroll et al., entitled "Orientation of Patient's Position Sensor using External Field"; U.S. Pat. No. 6,466,821 to Pianca et al., entitled "AC/DC Multi-Axis Accelerometer for Determining Patient Activity and Body Position;" U.S. Pub. No. 20150265839, entitled "Temperature Sensor for a Leadless Cardiac Pacemaker." An impedance sensor may be used to measure alterations of impedance through the chest cavity to determine changes in breathing. Respiration sensors such as impedance sensors may be used to monitor exertion and shortness of breath, which may be indicative of a myocardial infraction.

One or more interaction sensors 109 (discussed in further detail below) may be mounted on or within stimulation device 100 or otherwise in communication with stimulation device 100, in order to permit a user, such as the patient or a family member, to trigger a wireless communication connection 250 between stimulation device 100 and an external device 230. In certain embodiments, interaction sensors 109 may also be used to trigger activation of EGM storage.

Cardiac signals and other sensed signals may also be applied to the inputs of a data acquisition system 90 which is depicted as an analog-to-digital converter (ADC) for simplicity of illustration. EGM signals and other sensed signals are also applied to the inputs of an analog to digital (A/D) data acquisition system 490. The gain of the ADC converter 90 is controlled by the microprocessor 60 by signals along control line 92 in order to match the signal amplitude and/or the resolution to a range appropriate for the function of the ADC converter 90. The data acquisition system 90 may be configured to acquire intracardiac electrogram (EGM) signals, convert the raw analog data into digital signals, and store the digital signals for later processing and/or telemetric transmission (e.g., via wireless signals 250) to an external device 230 by way of telemetry circuit 424. Such a data acquisition system 90 may be coupled to the right atrial lead 20, the coronary sinus lead 24, and/or the right ventricular lead 30 through the switch 74 to sample the cardiac signals across any pair of desired electrodes.

The microcontroller 60 may further be coupled to a memory 94 by a suitable data/address bus 96, wherein the programmable operating parameters used by the microcontroller 60 may be stored and modified, as required, so as to customize the operation of the stimulation device 100 to suit the needs of particular patients. Such operating parameters may define, for example, stimulation pulse amplitude, pulse duration, polarity of electrodes, rate, sensitivity, automatic features, arrhythmia detection criteria, and/or the amplitude, shape of waves, and/or vector of each stimulation pulse to be delivered to the patient's heart 12 within each respective tier of therapy. The telemetry circuit 424 is activated by the microcontroller 60 by a control signal 106.

The operating parameters of implantable stimulation device 100 may be non-invasively programmed into the memory 94 through telemetry circuit 424 in telemetric communication with external device 230 or other external device, such as a programmer, transtelephonic transceiver, or a diagnostic system analyzer. The telemetry circuit 424 is activated by the microcontroller 60 by a control signal 106. The telemetry circuit 424 advantageously allows electrograms and status information relating to the operation of stimulation device 100 (as contained in the microcontroller 60 or memory 94) to be sent to external device 230 through an established communication link 250, and then on to a centralized processing system, where appropriate. The telemetry circuit 424 also allows a stimulation device 100 to include a patient-triggered activation option for electrogram storage. The telemetry circuit 424 permits communication between stimulation device 100 and external physiologic sensor(s) 108 located in other location(s) and/or other devices (e.g., drug pumps or patient worn/carried electronic devices or sensors).

The stimulation device 100 may additionally include a power source that may be illustrated as a battery 110 for providing operating power to all the circuits of FIG. 4B. For the stimulation device 100 employing shocking therapy, the battery 110 may be capable of operating at low current drains for long periods of time, such as, for example, less than 10 microamps (µA), and may also be capable of providing high-current pulses using shocking circuit 116 controlled by the microcontroller 60 via control signals 118 when the patient requires a shock pulse (e.g., in excess of 2 A at voltages above 2 volts (V) for periods of 10 seconds (s) or more).

In accordance with various embodiments disclosed below, the microcontroller 60 may also include a wireless communication control module 220, which may operate as the wireless communication control module 220 of FIG. 1.

Moreover, the wireless communication control module 220 may include an announcement timing control module 222 serving as the announcement timing control module 222 of FIG. 1. In such examples, the telemetry circuit 424 may be operated as the wireless communication interface 210 of FIG. 1, such as a Bluetooth® interface or another wireless communication interface implementing some wireless communication protocol or standard. In some embodiments, the announcement timing control module 222 may receive information from the atrial and ventricular sensing circuits 82, 84, the data acquisition system 90 (e.g., when an arrhythmia occurs), and/or the like, as well as other information available within the implantable stimulation device 100, either directly or via stored data in the memory 94, to determine a desired announcement frequency.

The microcontroller 60, in one embodiment, may perform the functions of the event detector 77, the timing control 79, the wireless communication control module 220, and/or other functions described herein by executing instructions stored in the memory 94. Accordingly, the microcontroller 60 may operate as the event detector 77 for periods of time, the timing control 79 for other periods of time, and so on. In some examples, the microcontroller 60 may operate as these particular functional blocks in a concurrent or parallel manner.

Additional and alternative details of implantable stimulation device 100 can be found in U.S. Pat. No. 5,405,363 (Kroll et al.) and U.S. Pat. No. 5,040,534 (Mann et al.), each of which are incorporated herein by reference in its entirety.

Event detector 77 may detect a preliminary indication of stroke based on an analysis of the output of heart activity detector 78, e.g., T-waves, U-waves (if present), ST segments, and QT segments, as described in U.S. Pat. No. 8,241,211 (Park), incorporated herein by reference.

U.S. Pat. No. 8,989,852 (Gill, et al.), incorporated herein by reference in its entirety, describes techniques that may be used in accordance with the present disclosure for detecting and distinguishing stroke and cardiac ischemia based on electrocardiac signals. In one example, the device senses atrial and ventricular signals within the patient along a set of unipolar sensing vectors and identifies certain morphological features within the signals such as PR intervals, ST intervals, QT intervals, T-waves, etc. The device detects changes, if any, within the morphological features such as significant shifts in ST interval elevation or an inversion in T-wave shape, which are indicative of stroke or cardiac ischemia. By selectively comparing changes detected along different unipolar sensing vectors, the device distinguishes or discriminates stroke from cardiac ischemia within the patient. The discrimination may be corroborated using various physiological and hemodynamic parameters.

Figure 5:
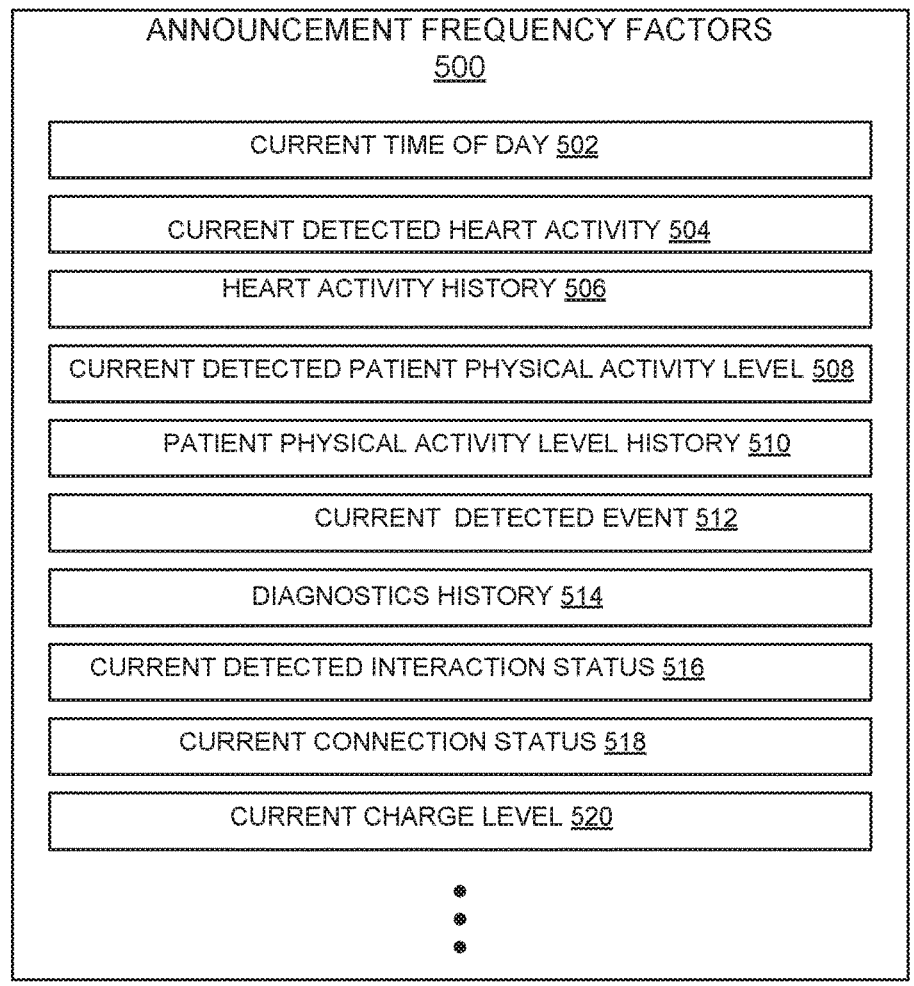
FIG. 5 is a list of example announcement frequency factors that may influence operation of the announcement timing control modules of FIGS. 4A and 4B.

FIG. 5 is a list of example announcement frequency (AF) factors 500 that may influence operation of the announcement timing control module 222 of FIGS. 1, 4A and 4B. Examples of the announcement frequency factors 500 may include, but are not limited to, a current time of day 502, a current detected heart activity 504 (e.g., heart rate, HRV or HRT, morphology, sinus rhythm, tachycardia, bradycardia, atrial fibrillation, ventricular fibrillation, asystole), a heart activity history 506, a current detected patient body position and/or physical activity level 508, a patient body position and/or physical activity level history 510, a current detected event 512 (e.g., myocardial infarction, stroke, cardiac ischemia, angina, neuropathic pain), a diagnostics history 514 (detected by an electronic device 200 or and/or programmed by a user), a current detected interaction status 516, a current wireless communication connection status 518, and a current battery charge level 520. Other factors 500 not listed in FIG. 5 (e.g., body temperature) may be employed, and some factors 500 depicted in FIG. 5 may not be employed when determining an appropriate announcement frequency.

The announcement timing control module 222 advantageously minimizes over-advertising by the electronic device 200 during periods when external device 230 is unlikely trying to connect, while improving the user experience during the connection process by increasing advertising/announcement frequency at times when a user is likely to initiate such a connection. In addition, announcement timing control module 222 advantageously increases connection speed between the electronic device 200 and external device 230 during critical periods, such as when the patient is experiencing an acute myocardial infarction or stroke, in order to enhance patient safety and clinical outcome. For example, embodiments herein, provide mechanisms to dynamically adjust advertising frequency based on, among other things, clinical conditions and system conditions in order to improve (e.g., optimize) communications needs and a preserve of battery power. In accordance with certain embodiments, a self-learning mechanism may be utilized to facilitate the process to improve the communications needs, while preserving battery power, thereby improving a user experience.

In an embodiment, the announcement timing control module 222 may base the announcement frequency at least in part on the current time of day 502. In one example, the electronic device 200 may include a real-time clock from which the current time of day 502 may be determined. In one example, a lower frequency may be used during times when the patient in which the electronic device 200 is implanted is expected to be asleep, such as approximately 10 PM to 6 AM, while a higher frequency may be utilized during times when the patient is expected to be awake. An expected time of sleep (e.g., 10 PM to 6 AM) and an expected time of wakefulness (e.g., 6:01 AM to 9:59 PM) may be programmed parameters entered by a user using an external device 230 and telemetry circuit 424 of electronic device 200. An expected time of sleep and an expected time of wakefulness may also be "learned" or modified by the electronic device 200, as discussed in more detail below. The particular times of day and their associated announcement frequencies may be configured by way of the telemetry circuit 424, or via other means. Also, the time of day 502 may be synchronized with the local time zone based on information received at the electronic device 200, such as information received via the wireless communication interface 201, such as telemetry circuit 424.

In certain embodiments, the announcement timing control module 222 may use current detected body position and/or physical activity level 508, such as posture, to confirm or corroborate a determination of announcement frequency based on current time of day. For example, a physiological sensor 108, such as an acceleration sensor, e.g., an accelerometer, may detect a patient's posture based on the acceleration of electronic device 200. If the patient is lying down, this may corroborate that a lower frequency may be used based on a current time of day 502 when the patient in which the electronic device 200 is implanted is expected to be asleep. If the patient is, however, not lying down based on, e.g., the accelerometer's reading, the announcement timing control module 222 may determine that a higher frequency of announcement should be used regardless of the current time of day 502. In this way posture, and/or other activity level data, may be used in conjunction with time of day in order to decrease the frequency of announcements at times when the patient is likely to be asleep, and thus unlikely to attempt communication with an external device.

In certain embodiments, the announcement timing control module 222 determines an expected time of sleep and an expected time of wakefulness by monitoring a patient over a baseline period of time, e.g., weeks or months, using physiological sensors 108 to log physical activity data with time of day into memory.

In certain embodiments, the announcement timing control module 222 keeps a log of the time of day 502 at which a user attempts to initiate a connection between the electronic device 200 and external device 230. Announcement timing control module 222 may use the log to determine trend information regarding the time of day that a user typically attempts to initiate such a connection. The announcement frequency may then be adjusted based on the trend data.

In some implementations, the announcement timing control module 222 may base the announcement frequency at least in part on the current detected heart activity 504 and/or the heart activity history 506. The announcement frequency control module 222 may interpret heart activity 504 such as a heart rate exceeding some threshold, tachycardia, HRV or HRT less than a threshold, certain morphologies, ST segment shifts less than a ST shift threshold, atrial fibrillation, ventricular fibrillation, and asystole, as conditions warranting increasing the announcement frequency to support faster creation of a wireless communication connection between the implantable stimulation device 100 and/or monitoring device 400 and the external device 230. In some examples, an abnormally low heart rate, such as one that falls below some threshold (e.g., indicative of Bradycardia, Sick Sinus Syndrome or profound long pauses), may also be considered pathological and/or unstable, prompting the announcement frequency control module 222 to increase the announcement frequency for at least some period of time after initial detection. Oppositely, a relatively normal or stable heart rate may influence the announcement frequency control module 222 to lower the current announcement frequency such as to conserve the electronic device's battery.

In certain embodiments, the announcement frequency may be dependent on duration of the detected heart activity 504. Announcement frequency may not be altered until the detected heart activity 504 has a duration longer than a threshold and announcement frequency may be increased in increments (in some embodiments, up to a limit) dependent on the duration of the detected heart activity 504 being longer than incrementally longer thresholds. For example, an AF lasting less than 5 minutes may not trigger an increase in announcement frequency. An AF lasting one hour or more may trigger a higher announcement frequency than an AF lasting between 5 minutes and an hour. In certain embodiments, an AF lasting more than an hour will not trigger any further increase in announcement frequency, unless other factors (either detected or programmed) are present.

In certain embodiments, electronic device 200 may tier the seriousness of the detected heart activity 504 and provide different announcement frequencies depending on the relative seriousness, e.g., the mode of advertising for a VF may be faster (e.g., every 1-10 seconds) than for a ventricular tachycardia (VT) (e.g., every 20-30 seconds) and the mode of advertising for a VT may be faster than for an atrial fibrillation (AF) (e.g., every 30-40 seconds). The ranking may also be dependent on other factors, such as those detected by physiological sensor 108 that may herald an acute episode or the patient's diagnostic history 514 (which may either be detected by the electronic device 200 or programmed by a user, e.g., prior stroke, myocardial infarction, ischemia, age CHADS2 score, etc.).

In some examples, the electronic device 200 (e.g., monitoring device 400 (FIG. 4A) and/or implantable stimulation device 100 (FIG. 4B)) may store previously sensed heart activities, such as heart rates, heartbeat waveforms, arrhythmias, and the like as heart activity history 506 in memory 494 (FIG. 4A) or 94 (FIG. 4B), and use this data to "learn" or predict times during the day when there is a higher probability of an abnormal heart activity to occur. The electronic device 200 may then increase the announcement frequency to support faster creation of a wireless communication connection between the electronic device 200 and the external device 230 during the periods when there is a higher chance of an abnormal heart activity so that the patient activator (external device 230) can be used immediately. Conversely, the electronic device 200 may decrease the announcement frequency to support slower creation of a wireless communication connection between the electronic device 200 and the external device 230 when there is a lower probability of an abnormal heart activity, e.g., to preserve battery function.

In some implementations, the announcement timing control module 222 may base the announcement frequency at least in part on the current detected patient physical activity level 508 and/or the patient physical activity level history 510. The patient physical activity level 508 (which may include positional data, e.g., prone or standing, blood pressure, and physical exertion data) may be determined by one or more factors sensed via one or more physiological sensors 108, which may be a motion sensor, accelerometer, gyroscope, temperature sensor, minute ventilation sensor, posture sensor, impedance sensors, optical sensors, oxygen saturation sensors, and the like. The possible presence of exercise-induced arrhythmia and/or other signs of relatively strenuous patient physical activity (e.g., fast walking, jogging, etc.), as indicated via the current detected patient physical activity level 508, may cause the announcement frequency control module 222 to increase the announcement frequency to support faster creation of a wireless communication connection between the electronic device 200 and the external device 230. More moderate indications of activity (e.g., slow walking) may lead the announcement control module 222 to determine that the announcement frequency should be relatively slow or moderate to conserve electrical power. Moreover, even lower levels of patient physical activity history (e.g., resting, reclining, sleeping for extended periods of time, and so on) may influence the announcement timing control module 222 to turn off announcements altogether for the time being. (For methods of detecting rest and sleep states using an activity sensor that may be used in accordance with the present disclosure, see U.S. Pat. No. 5,476,483, entitled "System and method for modulating the base rate during sleep for a rate-responsive cardiac pacemaker" (Bornzin et al.) which is hereby incorporated herein by reference.) Ceasing announcements under such circumstances may be seen as an automatic implementation of an "airplane mode" often provided in other wireless communication equipment.

In some embodiments, the electronic device 200 may store previously detected patient physical activity level history 510, against which the current detected patient physical activity level 508 data may be compared to ascertain whether the current patient physical activity level 508 is relatively high or low for the patient, thus providing some indication to the announcement timing control module 222 as to whether the current announcement frequency should be maintained or altered.

In another example, the announcement timing control module 222 may base the announcement frequency at least in part on a current detected event 512 and/or the diagnostics history 514. The current detected event 512 (e.g., VF episode, VT episode, AF episode, high voltage shock, a major ischemic event) may be determined by one or more factors sensed via the subcutaneous sensing circuits 482, the atrial sensing circuits 82, the ventricular sensing circuits 84, one or more physiologic sensors 108, and/or from the output of the heart activity detector 78. For example, during an out of clinic use environment, when a "critical" clinical condition occurs (e.g., a VF episode, a high voltage shock, a device delivery of a patient notification), the announcement timing control module 222 may increase the advertising frequency, increase the number of advertising pulses per advertising cycle, and/or decrease the pulse to pulse interval during the advertising cycle. Upon detection of a life-threatening event, such as an acute myocardial infarction or a stroke, the electronic device 200 increases the announcement frequency via the announcement timing control module 222 in response to such an episode. The increased advertising frequency, number of pulses and/or reduced pulse to pulse interval may be maintained for a pre-specified duration, after which, the announcement frequency is ramped back to an original or baseline duration, interval and number of pulse. During the increased advertising frequency/number of pulses, the user (e.g., the patient) has a higher chance of a successful connection (in a short period of time) between the implantable device and the application operating on an external device. Following the successful quick connection, information may be uploaded in a short period of time to the external device in order to afford remote care and contact with a clinician.

Embodiments herein allow patients to quickly communicate needed information to a caregiver. In addition, embodiments herein allow user initiate communications sessions to achieve a connection in a short period of time with a high success rate, thereby improving the usability of the system.

For example, when an indication of a heart attack is detected by the implantable device (e.g., acute ischemia), the device increases the announcement frequency to the fast advertising mode. An application operating on an external mobile device receives one or more advertising pulses, initiates a communication session and interrogates the implantable device. The application on the external device then sends the information collected from the implantable device to a remote care location, along with the location information for the external device (e.g., smart phone). The information concerning the event and the device location are automatically transferred to the remote care service without any patient involvement, given that at the time, the patient may not be able to initiate a follow-up session. The external device may also dial 911 or any other emergency phone number and provide a prerecorded message automatically and without patient involvement.

Additionally or alternatively, embodiments herein may be implemented in connection with non-critical clinical conditions that are not already designated as factors to start fast advertising (e.g., an AF episode, frequent retrograde conduction). A patient may feel a symptom (e.g., AF or retrograde conduction) and, in connection there with, direct an external device to initiate a communications session with the implantable device. When the patient exhibits a pattern of requesting communications sessions with the implantable device when certain symptoms occur, embodiments herein may use self-learning mechanisms to identify patient request patterns. When a patient experiences a symptom associated with a non-critical clinical condition, for which a patient request pattern indicates that the patient is likely to initiate a communications session, embodiments herein may change (e.g., increase) the announcement frequency. Through self-learning mechanisms, embodiments herein automatically determine to initiate fast advertising to facilitate user initiated follow-up for noncritical clinical conditions or other factors not designated for fast advertising thereby improving the usability of the system.

In some embodiments, the announcement timing control module 222 may base the announcement frequency at least in part on delivery of a patient notification by the implantable device. For example, the patient notification may be generated when the implantable device identifies a low battery condition, an abnormal lead impedance, a thoracic impedance outside an acceptable range, when the implantable device enters a backup mode, and the like. Additionally or alternatively, the patient notification may be generated in connection with a programmable function that is selected by the clinician. The patient notification may be auditory, vibratory and the like. The patient notification represents, among other things, that the patient should use an external device to initiate a communications session with the implantable device. When the patient notification is generated, the announcement timing control module 222 may increase the advertising frequency, increase the number of advertising pulses per advertising cycle, and/or decrease the pulse to pulse interval during the advertising cycle, among other things to adjust the announcement frequency.

In some embodiments, the announcement timing control module 222 may base the announcement frequency at least in part on time based communication, such as scheduled remote care follow up activity. For example, in connection with scheduled remote care follow up activity, it may be desirable for the implantable device to perform a nightly scheduled communications session with an external device (e.g., a bedside monitoring device, a smart phone, etc.). The remote care follow up activity may involve the implantable device initiating a communications session with the external device to download information (e.g., heart activity) for a period of time since the last download. Optionally, the communications session may include uploading new operating parameters to the implantable device.

In some examples, the external device 230 of FIGS. 1, 3A, 4A, and 4B may be a device that may be manually activated by the patient when the patient believes or feels that a heart-related clinical episode or pain-related episode has occurred. An indication of that activation may then be transmitted via a wireless communication connection 250 between the external device 230 and the electronic device 200. In some cases, the creation of a wireless communication connection 250 between the external device 230 and the electronic device 200 may be delayed due to the lack of an announcement message from the electronic device 200, such as due to a low announcement message frequency. Such a delay may thus cause an associated delay in the indication of patient activation being received at the electronic device 200. However, if the announcement timing control module 222 dynamically increases the announcement frequency in response to detecting the same clinical episode, generation of the wireless communication connection 250 may occur more quickly, thus reducing the delay in receiving the patient indication from the external device 230, thereby rendering the indication as a more effective patient confirmation of the clinical episode.

Additionally, the announcement timing control module 222 may access the diagnostics history 514 maintained by the monitoring device 400 and/or implantable stimulation device 100 to anticipate when next to advertise more frequently. The announcement timing control module 222 may compare the current heart activity status with previous detected heart clinical conditions to verify and/or accelerate announcement frequency. The announcement timing control module 222 may also store time of day 502 when a pathological heart activity is detected as part of the diagnostics history 514 in order to determine a trend in the data that may be used by announcement timing control module 222 to modulate advertisement frequency based on time of day.

In another example, the announcement timing control module 222 may base the announcement frequency at least in part on the current detected interaction status 516 of the electronic device 200. In one example, the electronic device 200 may include an interaction sensor 109 (FIGS. 4A and 4B), such as an accelerometer, that measures instantaneous acceleration of electronic device 200. In some embodiments, the announcement timing control module 222 may interpret high accelerations of short duration as a physical attempt by the patient or another person (e.g., a physical "tap" of the body near the electronic device 200) to increase the announcement frequency. In some examples, an increase in the announcement frequency may be initiated only upon the receipt of a predetermined sequence of taps detected via the interaction sensor 109 over some period of time. In other embodiments, the announcement frequency may be decreased by a different tap sequence.

In yet other examples, the physical tapping interaction between the patient or other person and the electronic device 200 may be detected using other sensors or transducers. For example, interaction sensor 109 may include an impedance monitor that may measure a voltage response to an induced current to determine if the impedance of a particular portion of the patient skin has been altered due to contact of the patient's hand with an area near the electronic device 200.

In yet another example, interaction sensor 109 may include an audio microphone or other sensor may be employed within the electronic device 200 to detect audible patient taps near the device 200. In yet another example, the announcement frequency may change based on the physical change of body position, such as from supine to upright.

In yet another embodiment, interaction sensor 109 may include a PPG sensor. For example, the implantable stimulation device 100 may incorporate one or more light sources, such as light-emitting diodes (LEDs) that emit light to a photo-detector. In this example, a change in the amount of light from the LEDs detected at the photo-detector may be interpreted as a patient tap of an area close to the device 100. A rhythmic tap will create a fluid shift that causes a rapid change in the optical absorption of the local tissue that is unlikely to occur for any reason other than patient initiation of the device.

In yet another embodiment, interaction sensor 109 may include one or more magnets employed to detect interaction between the patient and the implantable stimulation device 100.

The announcement timing control module 222 may base the announcement frequency at least in part on the current connection status 518 of the implantable stimulation device 100 in at least some embodiments. For example, if the current connection status 518 indicates that a wireless communication connection 250 is currently coupling the implantable stimulation device 100 with the external device 230, the announcement timing control module 222 may reduce the announcement frequency, or set the frequency to zero, at least while the wireless communication connection is active. In some embodiments, the announcement timing control module 222 may increase the announcement frequency for some determinable period of time following a disconnection of a wireless communication connection 250 to facilitate reconnection.

In addition, the announcement timing control module 222 may base the announcement frequency at least in part on the current charge level 520 of the battery 110 of the monitoring device 400 or implantable stimulation device 100 in some implementations. For example, relatively or extremely low charge levels of the battery 110 may cause the announcement timing control module 222 to reduce the frequency of the announcement messages, possibly to zero, for at least some period of time to conserve battery charge.

According to some embodiments, the announcement timing control module 222 may take into account a combination of the above factors 500 to determine an appropriate announcement frequency. For example, based on any or all of the heart activity history 506, the patient physical activity level history 510, and/or the diagnostics history 514, the announcement timing control module 222 may determine one or more times during the day that the patient is typically more active, as well as times during the day that the patient is more likely to experience a clinical episode, and increase the announcement frequency during at least some of those times of day, as indicated by the current time of day 502.

Various physiological parameters, hemodynamic parameters or cardiac rhythm parameters detected by the device can be used to confirm or corroborate the determination of whether the condition is stroke or cardiac ischemia, and also to confirm or corroborate changes in announcement frequency. For example, the heart rate can be monitored. An increase in heart rate is typically associated with stroke but not cardiac ischemia. As another example, heart rate variability (HRV) can be monitored. Reductions in HRV may be more pronounced from stroke than when cardiac ischemia occurs. Other parameters that can be monitored include signals representative of one or more of: blood volume; blood pressure; pre-ejection interval; heart rate turbulence (HRT), evoked response; capture threshold; kidney function; heart rate alternans, stroke volume and contractility. For example, a sudden increase in blood pressure may be due to cardiac ischemia and hence would tend to corroborate a diagnosis of ischemia. Pre-ejection intervals tend to become longer during cardiac ischemia but become shorter during stroke. Capture thresholds tend to increase due to cardiac ischemia, at least in the vicinity of the ischemia. Alternans tends to occur in conjunction with cardiac ischemia but not stroke. A variety of these parameters can be evaluated and then combined to yield a "score," which is then used to corroborate the determination of stroke vs. cardiac ischemia and may similarly be used by announcement timing control module 122 to corroborate whether announcement frequency should be modified and at what frequency.

Different days of the week, such as Monday through Friday versus Saturday and Sunday, may be distinguished such that the announcement frequency schedule may be different on weekdays versus weekends. For example, the heart activity level history 506, the patient physical activity level history 510, and/or the diagnostics history 514 may indicate that on the weekend the patient (a "weekend warrior") is exercising, which is inducing tachyarrythmias, but on the weekdays the patient is relatively sedentary, corresponding to periods of normal heart activity. Rather than treating all days equally and producing a weekly average based on time of day, the announcement timing control module 222 may distinguish between days of the week that could benefit from more or less frequent communication.

In other examples, an indication of elevated heart activity level or patient physical activity (e.g., by way of the current detected heart activity 504 and/or the current detected patient physical activity level 508), and/or an indication of an cardiac ischemia, myocardial infarction, stroke, angina, or episode of pain (e.g., via the current detected event 512) may cause the announcement timing control module 222 to increase the announcement frequency, even though the current time of day 502 would otherwise dictate a relatively lower announcement frequency. In some implementations, a physical tap by a patient, as indicated via the current detected interaction status 516, may also cause an increase in the announcement frequency despite a current time of day 502 indicating a lower frequency and a lack of any elevated heart or patient physical activity and an absence of any event, as described above (e.g., when the patient has vasovagal symptoms that are not associated with abnormal cardiac rhythms). Thus, one or more announcement frequency factors 500 may override another one or more of the announcement frequency factors 500, thus implementing a hierarchy among the factors 500.

In another specific example, one or more physiological sensors 108 (shown in FIGS. 4A and 4B) acquires a current detected patient physical activity level 508 over a predetermined period of time (e.g., an hour, four hours, eight hours, a day and the like). For instance, an accelerometer or an activity sensor may be used to sense body movements of the patient. Alternatively, the activity sensor may be a workload sensor or any other type of sensor that senses metabolic changes, such as nutrition and oxygen consumption of the patient. Current detected patient physical activity level 508 data is analyzed to determine whether a state of sustained exercise has been achieved. The state of sustained exercise is declared when the level of activity is greater than a predetermined exercise threshold value (e.g., greater than 130% of at rest level) warranting modulation of announcement frequency. Alternatively, the sustained exercise state may be described when the current detected patient physical activity level 508 is less than the predetermined exercise threshold value, but the activity level remains at an intermediate threshold level for a predetermined length of time (e.g., at 75% of the exercise threshold value for a sustained duration of five minutes, 20 minutes and the like). As a further alternative, the sustained exercise state may be declared when the activity level increases by a large incremental amount in a short period of time. The current detected patient physical activity level 508 may be stored in memory 94 for later retrieval and processing and/or may be used by announcement timing control unit 222 to trigger an increase in announcement frequency.

Optionally, the current detected patient physical activity level 508 may be compared to an activity level baseline value. The baseline of the activity level data may be determined over a predetermined period of time (e.g., one hour). The activity level data, to determine the baseline, may be collected when the patient is minimally exerting herself. For example, a patient may be walking at a non-exercise pace for the baseline predetermined period of time. The baseline may be an average of multiple values of a patient's activity over multiple predetermined periods of time (e.g., one hour periods measured weekly). Alternatively, the baseline activity may be acquired only once in a longer period of time (e.g., once every six months) while the activity level data is acquired more often.

In an embodiment, as the patient exercises, current detected heart activity 504 data, which includes, e.g., ST segments, arrhythmias, heart rate, etc. is acquired. The current detected heart activity 504 data is collected over a series of cardiac cycles for a predetermined period of time. For instance, the current detected heart activity 504 data may be collected over a ten minute or one hour sample interval. The current detected heart activity 504 data may be a series of intrinsic heartbeats. Alternatively, the current detected heart activity 504 data may be a series of paced heartbeats, which are stimulated by either an atrial pulse generator or a ventricular pulse generator. Further, the current detected heart activity 504 data may be collected before, concurrently with, or after the current detected patient physical activity level 508.

In an embodiment, an ST baseline may be determined based on the ST segment variations in the cardiac data. The ST baseline may be determined by collecting cardiac data when the patient is resting and not moving (e.g., sitting or lying down). The baseline may be based on data collected over a baseline predetermined period of time (e.g., an hour, four hours, a day and the like).

When detected patient physical activity level 508 is above a threshold, microcontroller 460 (FIG. 4A) or 60 (FIG. 4B) may monitor the cardiac data (which may take more battery energy to detect) for, e.g., ST segment variations, such as ST shifts and ST deviations, as described above, and event detector 77 determines a current detected event 512, such as ischemic episodes (e.g., ischemia, demand ischemia, acute myocardial infarction, stroke, an inconsistent physiology, and the like). Depending on the seriousness of the ischemic episode detected by event detector 77, the frequency of announcements may be increased and/or the patient physical activity level that induced the ischemia may be recorded in memory 94. Alternatively, a detected patient physical activity level that is a running average of activity level data from the time of beginning exercise or from the time of the last ischemic episode may be recorded. Further heart activity and patient physical activity level data may be recorded at the time of the ischemic episode, such as, heart rate, pacing rate, blood pressure, respiratory rate, oxygen consumption, carbon-dioxide production, body motion, and the like that may corroborate the detected event and modulate announcement frequency.

For example, microcontroller 460 or 60 may determine whether the patient abruptly stopped exercising. For example, microcontroller 460 or 60 monitors the physiologic sensor 108 (e.g., accelerometer) for any significant measurement drop over a predetermined window of time (e.g., the measurement drop may be based on a percentage drop). For instance, the patient may have stopped exercising immediately upon having the ischemic episode because of anginal pain (e.g., a change in body posture immediately following an ischemic episode). In the case where the electronic device 200 is a neurostimulator, the patient may have stopped exercising based upon neurogenic pain, and the device will record these instances as well in order to determine trends, as discussed in further detail below. Alternatively, the patient may indicate an amount of anginal pain (or neurogenic pain) by tapping their body proximate to the electronic device 200 location. Microcontroller 460 or 60 may also monitor for a sudden increase in heart rate or other change in the patient's movement characteristic of acute pain. If the patient stopped exercising after the ischemic episode or there is a similar indication, the event detector 77 may detect pain and increase advertisement frequency in anticipation of the patient triggering connection of the external device with the electronic device.

Microcontroller 460 or 60 may also log whether or not the patient attempted such a connection even in the absence of device detected anginal or neurogenic pain. Also, the external device (e.g., through an app) may prompt the patient to enter the reason why the patient triggered the device (e.g., angina pain, neurogenic pain, palpitations, syncope, etc.) and this information may be programmed into the electronic device 200 and logged with the detected heart activity and/or detected patient physical activity and stored in memory 494 (FIG. 4A) or 94 (FIG. 4B). In this way, electronic device 200 records in memory (e.g., 94 or 494) that a detected heart activity and/or detected patient physical activity level is accompanied by an event, e.g., that an ST shift is accompanied by anginal pain. Microcontroller 460 or 60 may also log the time of day 502 at which a detected heart activity and/or detected patient physical activity level is accompanied by an event. However, if the patient did not stop exercising during an ischemic episode and there is no other indication of an episode, such as angina, the electronic device 200 records in memory 94 or 494 that the heart activity, e.g., ST shift, is not accompanied by anginal pain or other episode.

The microcontroller 60 and/or 460 may determine current detected patient physical activity level 508 based on the activity level value at the occurrence of the ischemic episode or other event 512. Alternatively, the current detected patient physical activity level 508 may represent a running average of the activity level when the ischemic episode or other event occurred. Over a predetermined period of time (e.g., several weeks or months), trends may be determined based on the heart activity history 506, the patient physical activity level history 510, the time of day 502 at which a detected heart activity and/or detected patient physical activity level is accompanied by an event, diagnostic history 514 and/or history of interaction/connection requests. These trends may indicate heart activities and patient physical activity level that are either likely to trigger an event or prompt a patient to try establish a connection between devices and time of day when events are more likely to occur or a patient is more likely to attempt a connection between devices.

The announcement timing control module 222 may also access configuration data, such as in the memory 94 and/or 494, that indicates preferences regarding, for example, which announcement frequency factors 500 override other factors 500, what levels detected by the interaction sensor 109 are to be interpreted as a physical tap by the patient, what levels of patient or heart activity are to be attained before the announcement frequency is increased, how many different announcement frequencies are to be employed, and so on.

Figure 6:
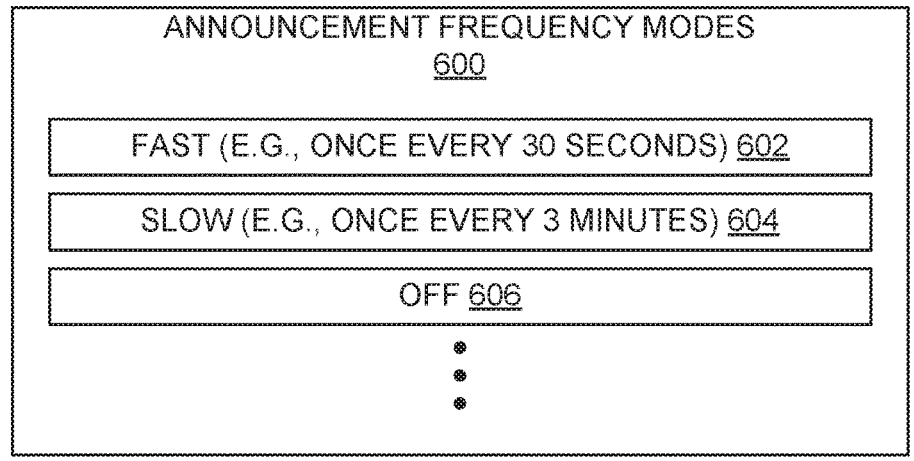
FIG. 6 is a list of example announcement frequency modes that the announcement timing control modules of FIGS. 4A and 4B may provide based on the announcement frequency factors of FIG. 5.

FIG. 6 is a list of example announcement frequency modes 600 or states that the announcement timing control module 222 of FIGS. 1, 4A, and/or 4B may provide based on the announcement frequency factors 500 of FIG. 5. As shown in this particular example, three separate modes are utilized: a "fast" frequency mode 602, a "slow" frequency mode 604, and an "off" mode 606. In one implementation, the fast frequency mode 602 may result in an announcement message, data packet, or other signal being transmitted via the telemetry circuit 424 once every 30 seconds, and the slow frequency mode 604 may result in an announcement frequency of three minutes. In other embodiments, greater or fewer numbers of announcement frequency modes 600 may be employed, as well as different announcement frequencies for each of the modes 600. Moreover, some examples may not implement the off mode 606 (during which no announcement messages, data packets, or other signals are transmitted) unless an override mechanism, such as by way of a physical tap by the patient, as described above, is available to initiate the wireless communication connection 250 in the absence of an announcement.

Figure 7:
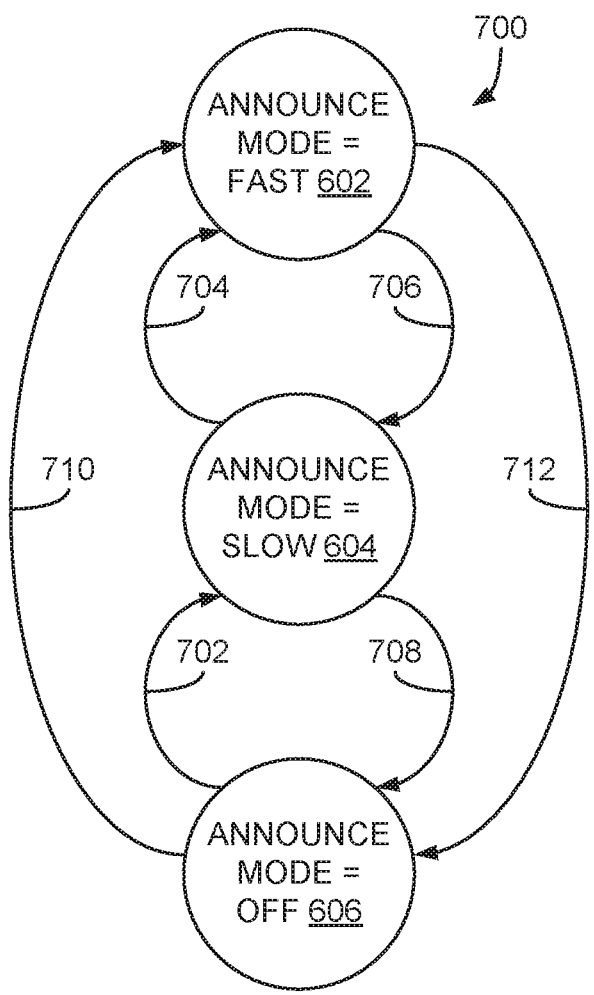
FIG. 7 is an example state diagram of the example announcement frequency modes of FIG. 6.

FIG. 7 is an example state diagram 700 of the example announcement frequency modes 600 of FIG. 6. In an example, the state diagram 700 represents a state machine implemented within the announcement timing control module 222. In the example of FIG. 7, the state machine may be a Moore state machine, in which the current announcement frequency is dictated by the current state or mode 602, 604, and 606. In other examples, a Mealy state machine may be implemented, in which the current announcement frequency associated with a specific state or mode 602, 604, or 606 may be altered based on values of the announcement frequency factors 500.

The state diagram 700 includes several state transitions 702, 704, 706, 708, 710, and 712 from one of the states 602, 604, and 606 to another based on current values of the announcement frequency factors 500. In other embodiments, one or more of the transitions 702-712 may be omitted. Also, in some embodiments, a transition from the off mode 606 may be to either the slow mode 604 by way of transition 702 or to the fast mode 602 via transition 710, depending on the current state of one or more of the announcement frequency factors 500. For example, the occurrence of a clinical episode, as indicated by the current detected event 512, or the detection of a physical tap via the current detected interaction status 516, may cause the announcement timing control module 222 to use transition 710 from the off mode 606 to the fast mode 602, or to use transition 704 from the slow mode 604 to the fast mode 602, to create a wireless communication connection 250 quickly. Similarly, a transition from the fast mode 602 may be to either the slow mode 604 by way of transition 706 or the off mode 606 via transition 712.

Figure 8:
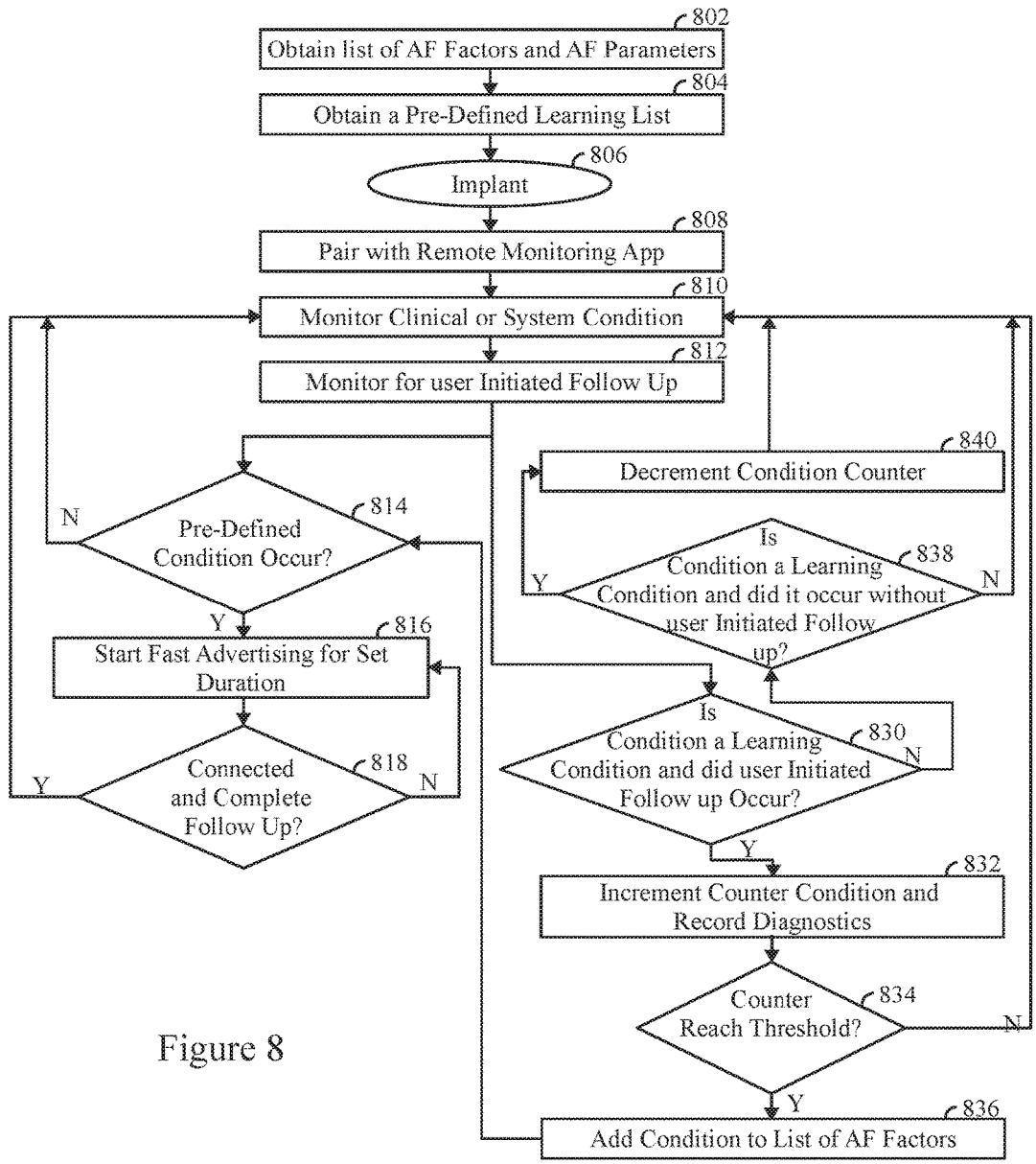
FIG. 8 is a simplified flow diagram of an example method of operating the electronic device of FIG. 1 to employ dynamic announcing for creation of wireless communication connections

FIG. 8 is a simplified flow diagram of an example method of operating the electronic device of FIG. 1 to employ dynamic announcing for creation of wireless communication connections. While the method 800 is described below within the context of the announcement timing control module 222 of the wireless communication interface control module 220 of the electronic device 200 of FIG. 1, other circuits or systems may employ the method 800 in accordance with embodiments.

In the method 800, the announcement timing control module 222 may set an initial frequency for transmission of announcement messages, data packets, or other signals (operation 302). In some examples, the frequency may define an advertisement cycle that includes X advertisement pulses, that are separated by a pulse to pulse interval of Y, where the advertisement cycle is repeated every Z seconds or minutes. Additionally or alternatively, in other examples, the announcement timing control module 222 may not set an initial transmission frequency for the announcements. For example, no announcement messages may be sent for select periods of time.

As explained below in more detail, the method 800 dynamically adjusts the announcement frequency (e.g., advertising frequency, pulse to pulse interval, number of pulses/cycle) based on various announcement frequency factors such as clinical conditions, time base communication, self-learning patterns for user initiated follow up sessions and/or system conditions, all of which represent characteristics of an environmental external of the electronic device. The method 800 may utilize self-learning to manage the communications needs and the preservation of battery power. The electronic device is implanted, and then paired with an external device for remote monitoring and/or set up for MRI scanning readiness. The electronic device will continue to monitor a set of pre-defined AF factors, such as adjustable clinical conditions (e.g., high voltage shock, patient notification delivery), system conditions and/or other factors. When the electronic device detects a pre-defined AF factor (e.g., clinical condition such as a patient notification being delivered, system condition and/or other factor), the electronic device commands the wireless communications interface 210 (FIG. 2) to increase the announcement frequency to a new pre-defined announcement frequency. The AF factors represent characteristics of the environment external to the electronic device.

Each announcement frequency is defined by one or more adjustable parameters. Non-limiting examples of the adjustable parameters are to increase the number of advertising pulses/cycle, increase the advertising frequency between cycles and/or decrease the pulse to pulse interval between the advertising pulses and the like. The advertisement pulses are transmitted at the increased advertising frequency and/or number of pulses, for a predefined duration (e.g., 15 minutes). When a connection is established, the announcement parameters are reset to the original or baseline values. In the event that no connection is established before expiration of the predefined duration, the announcement parameters are also reset to the original or baseline values. In accordance with an embodiment, the announcement parameters are reset to the original or baseline values at the expiration of the predefined duration.

Optionally, at the expiration of the predefined duration, the announcement parameters may be successively adjusted over a range between the new/faster and the baseline values, such that the electronic device gradually slowing down the advertising frequency and/or gradually reduces the number of adverting pulses/cycle. The rate at which the announcement parameters are adjusted between the new/faster values and the baseline values may be defined by a pre-defined ramp-down rate.

As one nonlimiting example, the announcement frequency may be adjusted (e.g., increased) each time a new patient notification is generated and/or each time a clinical condition occurs. In connection with time based remote follow up, the method 800 will increase the advertising frequency and number of advertising pulses shortly before the scheduled time of remote follow up.

The method 800 begins at 802, where one or more processors obtain a list of predefined AF factors and AF parameters. At 804, the one or more processors obtain a predefined learning list that is developed in connection with a self-learning mechanism as explained herein. The predefined learning list includes a list of one or more clinical conditions, system conditions or other factors, for which a pattern has been identified associating with the condition with user initiated communications sessions. The factors on the predefined learning list represent characteristics of the environment external to the implantable device that, when detected, indicate a high probability that the user will shortly thereafter initiate a communication session between an external device and the implantable device.

At 806, the implantable device is implanted, and at 808 the one or more processors pair the implantable device with a monitoring application operating on a remote external device. Thereafter, an iterative loop is implemented within the implantable device by the one or more processors to monitor for AF factors.

At 810, the one or more processors monitor and identify characteristics external to the implantable device for a clinical or system condition of interest. Optionally, the processors may monitor and identify other characteristics discusses herein as AF factors. When a clinical or system condition of interest is detected, flow moves to 812. At 812, the one or more processors determine if a user initiated follow-up occurs contemporaneous (e.g., within a defined window before or after) with identifying the condition. Following 812, parallel paths may branch to 814 and 830.

At 814, the one or more processors determine whether the clinical or system condition that was identified at 810 represents a predefined condition associated with an AF factor on the list obtained at 802. When the condition identified at 810 corresponds to a predefined condition from the list of AF factors, flow moves to 816. Otherwise, flow returns to 810.

At 816, the one or more processors adjust the announcement frequency to correspond to the announcement frequency defined by the AF parameters associated with the AF factor identified. As explained herein, at 816, the announcement frequency may be adjusted to start a fast advertising session having one or more of an increased advertising frequency, number of pulses per advertising cycle and/or shorter pulse to pulse intervals. The fast advertising session is maintained for a duration defined by the AF parameters. Optionally, multiple different fast advertising sessions may be stored for corresponding different AF factors (e.g., one frequency for a VT episode, another frequency for patient notifications).

At 818, the one or more processors determine whether a successful connection has been initiated between the electronic device and the external device. When a successful connection is achieved, flow returns to 810. Otherwise, flow returns to 816. The operations at 816-818 are iteratively repeated for the duration of the fast advertising session. At the expiration of the fast advertising session, the one or more processors ramp down the announcement frequency to return to the original or baseline announcement frequency. Thereafter, flow returns to 810 where the one or more processors monitor for a new condition of interest.

The operations at 830-840 represent an optional self-learning path that may be followed in parallel with the operations at 814-818. Optionally, the self-learning path at 830-840 may be omitted entirely. At 830-840, the one or more processors track user initiated follow-up sessions to determine whether certain types of "learning" conditions should be added to or removed from the list of AF factors. At 830, the one or more processors determine i) whether the condition is an "learning" condition and ii) whether contemporaneous a user initiated follow-up was identified at 812 in connection with the condition identified at 810. When a user initiated follow-up is identified at 812, flow moves to 832. At 832, a counter is incremented in connection with the learning condition and the information is recorded as diagnostic information. At 834, the one or more processors determine whether the counter has reached a threshold. The threshold is utilized by embodiments herein as a determination of whether a pattern exists associating user initiated sessions with the occurrence of a condition. When the count reaches the threshold, flow moves to 836 where the condition is added to the list of AF factors. Otherwise, at 834, when the counter does not reach the threshold, flow returns to 810 where the one or more processors continue monitoring for the next condition.

Returning to 830, when the one or more processors determined that either the condition identified at 810 did not represent a "learning" condition and/or the learning condition did not occur with a user initiated follow-up, flow moves to 838. At 838, the one or more processors determine whether the condition represents a learning condition. When the condition represents a learning condition, that occurred without user initiated follow-up, flow moves to 840. At 840, the one or more processors decrement the counter associated with the condition. By decrementing the counter, the processors record the fact that the user did not perform a user initiated follow-up in connection with a condition otherwise considered a learning condition. At 838, when the condition does not represent a learning condition, the counters are not incremented or decremented and instead flow returns to 810 to monitor for the next condition.

In accordance with the operations at 830-840, when the self-learning mechanism is activated, the system starts to track the user initiated follow ups. The clinical conditions are categorized and countered. If a counter/s is increased above a pre-defined threshold, the system designates that the fast announcement frequency is to be used for the associated clinical condition/s. The condition is added to the list of announcement frequency factors. The next time, when the same clinical condition occurs, the system will automatically increase the announcement frequency. Conversely, when a clinical condition no longer results in a user initiated follow-up, the clinical condition is removed from the list of fast announcement frequency factors.

As a nonlimiting example, a patient may feel a palpitation or shortness of breath. In response, the patient may attempt to contact a doctor and report a situation and initiate an uploading session from the implantable device to an external device. When using the baseline announcement frequency, a longer period of time may pass before a connection is established and the information is uploaded. The communication session may not occur until after the clinical condition has stopped and thus the information uploaded may not capture all of the relevant clinical information (e.g., associated with a short run of a PVC that may lead to a PMT). Given that the uploaded information may not include all of the relevant clinical information, the clinician may choose to observe whether the patient experiences the same symptom again at a later point in time.

In accordance with embodiments herein, the self-learning mechanism records the patient's attempt to connect. After one or more repeated instances of the situation, embodiments herein learn that, when a short run of a PVC occurs that leads to a PMT, a high likelihood exist that the patient will perform a user initiated follow-up. Embodiments herein will designate the related physiologic condition as an AF factor and, when next experienced, will automatically initiate a fast advertising session. Accordingly, when the patient next feels a palpitation or shortness of breath, the implantable device has automatically increased the announcement frequency. In connection there with, a communication session is established in a relatively short period of time and the relevant physiologic information is uploaded in real time to capture the full clinical event.

As another example, the self-learning mechanism may be utilized to dynamically adjust the announcement frequency in connection with regular daily transmissions. For example, standard connection times may be recorded. When a pattern is identified from the connection times (e.g., once per day), an AF factor may be defined to correspond to the particular time of day. Optionally, embodiments herein may calculate a distribution of the connections for regular remote follow-up. When regular remote follow-ups are identified, an advertisement window may be defined surrounding the predicted time of the remote follow-up. During the advertisement window, the announcement frequency may be adjusted to a fast advertising session while reducing the announcement frequency outside of the window.

While the embodiments described in detail above focus on implantable medical devices, other medical electronic devices that are not implantable, such as a "wearable" medical device that may monitor for heart rate, arrhythmia and/or other medical conditions, may serve as the electronic device 200, and may incorporate any of the aspects of the embodiments discussed above. Moreover, in some examples, the electronic device 200 may not be a medical device, whether implantable or not, but may still incorporate one or more of the aspects of the embodiments described herein.

Those skilled in the art will understand and appreciate that various modifications not explicitly described above may be made to the present disclosure and still remain within the scope of the present invention. Moreover, although the present invention has been described with reference to preferred embodiments, persons skilled in the art will recognize that changes may be made in form and detail without departing from the scope of the present invention.

What is claimed is:

1. An implantable electronic device configured to be implanted in a patient and configured to communicate wirelessly with an external device separate from the implantable electronic device, the implantable electronic device comprising:
    a wireless communication interface configured to transmit announcement signals used to create a wireless communication connection with the external device;
    one or more sensors used to monitor one or more clinical conditions associated with the patient; and
    a microcontroller configured to
        monitor for one or more specific changes in at least one of the one or more clinical conditions associated with the patient that is/are being monitored using at least one of the one or more sensors, and
        dynamically control timing of the announcement signals in response to detecting at least one of the one or more specific changes being monitored for by the microcontroller.

2. The implantable electronic device of claim 1, wherein:
    the implantable electronic device comprises at least one of an automatic implantable cardioverter defibrillator, an artificial cardiac pacemaker, or an implantable loop recorder;
    the at least one of the one or more sensors is configured to sense a signal indicative of cardiac activity of the patient's heart; and
    the at least one of the one or more specific changes in the at least one of the one or more clinical conditions is monitored for by the microcontroller using the signal indicative of cardiac activity of the patient's heart.

3. The implantable electronic device of claim 1, wherein the one or more sensors comprise one or more of the following:
    an electrogram sensor;
    a photoplethysmography sensor;
    a thoracic impedance sensor;
    a minute ventilation sensor;
    an activity sensor;
    a temperature sensor;
    a posture sensor; or
    an oxygen saturation sensor.

4. The implantable electronic device of claim 1, further comprising a real-time clock configured to provide a current time of day, and the microcontroller further configured to dynamically control the timing of the announcement signals based on the current time of day.

5. The implantable electronic device of claim 1, wherein the at least one of the one or more sensors comprises at least one of an accelerometer or a gyroscope, and wherein the at least one of the one or more specific changes in the at least one of the one or more clinical conditions associated with the patient is monitored for by the microcontroller using at least one of the accelerometer or the gyroscope.

6. The implantable electronic device of claim 1, wherein the at least one of the one or more specific changes in the at least one of the one or more clinical conditions associated with the patient comprises a change in heart activity, and wherein the microcontroller dynamically controls timing of the announcement signals based on at least one of a detected arrhythmic episode, a therapy delivered in response to the detected arrhythmic episode, or a patient notification delivered in response to the detected arrhythmic episode.

7. The implantable electronic device of claim 6, wherein the microcontroller dynamically controls timing of the announcement signals based on at least one of a detected ventricular fibrillation (VF) episode, a high voltage shock delivered in response to the detected VF episode, or a patient notification delivered in response to the detected VF episode.

8. The implantable electronic device of claim 1, wherein in order to dynamically control the timing of the announcement signals the microcontroller is configured to at least one of i) increase an advertising frequency, ii) increase a number of advertising pulses per advertising cycle, or iii) decrease a pulse to pulse interval during the advertising cycle.

9. The implantable electronic device of claim 1, wherein the at least one of the one or more sensors is configured to monitor heart activity, and wherein the microcontroller is configured to dynamically increase or decrease the frequency of the announcement messages in response to detecting a specific change in the heart activity.

10. The implantable electronic device of claim 1, wherein the at least one of the one or more sensors is configured to monitor heart rate, and wherein the microcontroller is configured to increase the frequency of the announcement messages in response to the heart rate exceeding a first threshold or falling below a second threshold.

11. The implantable electronic device of claim 1, wherein the one or more sensors is/are configured to monitor at least one of a body position, or a physical activity level, and wherein the microcontroller is also configured to increase the frequency of the announcement messages in response to at least one:
    the body position being an upright position, or
    the physical activity level exceeding a threshold.

12. The implantable electronic device of claim 1, wherein the one or more sensors is/are configured to monitor at least one of a body position, or a physical activity level, and wherein the microcontroller is also configured to cease transmission of the announcement messages in response to at least one:
    the body position being a supine position, or
    the physical activity level being indicative of the patient sleeping.

13. The implantable electronic device of claim 1, wherein the microcontroller is also configured to predict when to change a timing of the announcement signals based on the at least one of the one or more clinical conditions associated with the patient monitored using the at least one of the one or more sensors.

14. The implantable electronic device of claim 13, wherein the microcontroller is configured to predict when to change the timing by identifying a pattern associating user-initiated follow-up sessions and occurrence of a clinical condition.

15. The implantable electronic device of claim 1, wherein:
the microcontroller is configured to use the at least one of the one or more sensors to monitor heart activity of the patient;
the implantable electronic device includes a memory configured to store heart activity information together with a time of day at which the heart activity information was detected;
the microcontroller is configured to determine a trend in the time of day at which a pathological heart activity is detected; and
the microcontroller is further configured to dynamically set the frequency of the announcement messages based on the trend.

16. The implantable electronic device of claim 1, wherein:
the microcontroller is configured to use the at least one of the one or more sensors to monitor heart activity of the patient and determine whether the heart activity is a pathological heart activity and monitor for one or more cardiac events;
the implantable electronic device further comprises a memory configured to store at least one of the pathological heart activity and the cardiac event together with the time of day at which at least one of the pathological heart activity and the cardiac event was detected;
the microcontroller is configured to determine a trend in the time of day at which at least one of the pathological heart activity or at least one of the one or more cardiac events is detected; and
the microcontroller is further configured to dynamically set the frequency of the announcement messages based on the trend.

17. The implantable electronic device of claim 1, wherein:
the microcontroller is configured to use the at least one of the one or more sensors to monitor heart activity of the patient and monitor for one or more cardiac events;
the implantable electronic device further comprises a memory configured to store at least one of the heart activity or at least one of the one or more cardiac events when the patient triggers the implantable electronic device to connect with the external device;
the microcontroller is configured to determine a trend in at least one of the heart activity or the cardiac event occurring when the patient triggers the implantable electronic device to connect with the external device; and
the microcontroller is further configured to increase the frequency of the announcement messages when at least one of a current detected heart activity and a current detected cardiac event satisfies the trend.

18. An implantable medical device for monitoring physiology of a person, the implantable medical device capable of wirelessly communicating with an external device located external to the person, the implantable medical device comprising:
a wireless communication interface configured to transmit announcement signals used to create a wireless communication connection with the external device;
one or more sensors used to monitor one or more system conditions associated with the implantable medical device; and
a microcontroller configured to
monitor for one or more specific changes in at least one of the one or more system conditions associated with the implantable medical device being monitored using at least one of the one or more sensors, and
dynamically control timing of the announcement signals in response to detecting at least one of the one or more specific changes being monitored for by the microcontroller.

19. The implantable medical device of claim 18, wherein one of the one or more sensors comprises a sensor configured to detect a level of acceleration imparted upon the implantable medical device, and wherein the microcontroller is also configured to increase the frequency of the announcement messages based on the detected level of the acceleration exceeding a threshold.

20. The implantable medical device of claim 18, wherein the one of the one or more system conditions associated with the implantable medical device, which is monitored for by the microcontroller, relates to a battery charge level, and wherein the microcontroller is configured to dynamically control the timing of the announcement signals based on the battery charge level.

21. The implantable medical device of claim 18, wherein the one or more specific changes in at least one of the one or more system conditions associated with the implantable medical device, which is monitored for by the microcontroller, relates to a lead impedance, and wherein the microcontroller is configured to dynamically control the timing of the announcement signals based on an abnormal lead impedance being detected.

22. A method for dynamically controlling timing of advertising messages transmitted by an implantable electronic device to create a wireless communication connection with an external device separate from the implantable electronic device, the method comprising:
monitoring for one or more specific changes in at least one of one or more clinical conditions associated with a patient within which the implantable electronic device is implanted; and
dynamically controlling timing of the advertising messages by setting at least one of i) a frequency of the advertising messages, ii) a number of advertising pulses per advertising cycle, or iii) a pulse to pulse interval during the advertising cycle, in response to detecting at least one of the one or more specific changes; and
transmitting the advertising messages using results of the setting.

23. The method of claim 22, wherein the at least one of the one or more specific changes in at least one of the one or more clinical conditions associated with the patient being monitored for comprises at least one of specific change in a heart rate, detection of a specific cardiac event, detection of a specific neurogenic event, a specific change in body position, or a specific change in physical activity level.

24. The method of claim 22, further comprising providing a current time of day using a real-time clock, and wherein the setting is also performed at least in part based on the current time of day.

* * * * *